United States Patent
Badone et al.

[11] Patent Number: 5,981,754
[45] Date of Patent: Nov. 9, 1999

[54] 4-ARYL-1-PHENYLALKYL-1,2,3,6-TETRAHYDROPYRIDINES HAVING NEUROTROPHIC AND NEUROPROTECTIVE ACTIVITY

[75] Inventors: Domenico Badone, Induno Olona; Marco Baroni, Vanzago; Rosanna Cardamone, Como, all of Italy; Jacqueline Fournier, Plaisance-du-Touch, France; Umberto Guzzi, Milan; Alessandra Ielmini, Arsago Seprio, both of Italy

[73] Assignee: Sanofi, Paris, France

[21] Appl. No.: 08/973,712

[22] PCT Filed: Jun. 26, 1996

[86] PCT No.: PCT/FR96/00995

§ 371 Date: Feb. 24, 1998

§ 102(e) Date: Feb. 24, 1998

[87] PCT Pub. No.: WO97/01536

PCT Pub. Date: Jan. 16, 1997

[30] Foreign Application Priority Data

Jun. 28, 1995 [FR] France ................... 95 07760

[51] Int. Cl.$^6$ ............ C07D 211/70; C07D 401/04; C07D 211/52; A61K 31/445
[52] U.S. Cl. ............ 546/193; 546/192; 568/309
[58] Field of Search ............ 546/193, 192; 568/309

[56] References Cited

FOREIGN PATENT DOCUMENTS

| 0 398 578 | 11/1990 | European Pat. Off. |
| 0 412 901 | 2/1991 | European Pat. Off. |
| 0 458 696 | 11/1991 | European Pat. Off. |
| 43 25 855 | 2/1995 | Germany |
| 48 006 471 | 2/1973 | Japan |
| 93 11107 | 6/1993 | WIPO |

OTHER PUBLICATIONS

Rehse et al., *Arch. Pharm.*, vol. 312, 1979, pp. 670–681.
El–Shafie et al., *Sci. Pharm.*, vol. 62, 1994, pp. 389–403.
Sato et al., *Chem. Pharm. Bull.*, vol. 29, 1981, pp. 3134–3144.
Saari et al., *J. Med. Chem.*, vol. 27, No. 9, 1984, pp. 1182–1185.
Suzuki et al., *Synthetic Communications*, vol. 11, No. 7, 1981, pp. 513–519.
Galda et al., *Synthesis*, vol. 5, 1996, pp. 614–620.
Huth et al., *Tetrahedron*, vol. 45, No. 21, 1989, pp. 6679–6682.
Siegmann et al., *Organometallics*, vol. 8, No. 11, 1989, pp. 2659–2664.

*Primary Examiner*—Zinna Northington Davis
*Attorney, Agent, or Firm*—Bacon & Thomas PLLC

[57] ABSTRACT

The present invention relates to the compounds of formula (I)

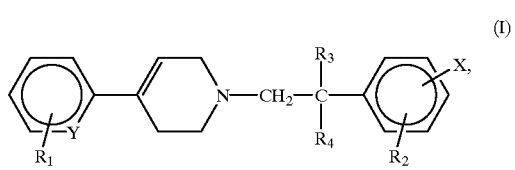

wherein Y is —CH— or —N—; $R_1$ is hydrogen, a halogen or a $CF_3$, $(C_3-C_4)$alkyl or $(C_1-C_4)$alkoxy group; $R_2$ is hydrogen, a halogen, a hydroxyl or a $CF_3$, $(C_3-C_4)$alkyl or $(C_1-C_4)$alkoxy group; $R_3$ and $R_4$ are each hydrogen or a $(C_1-C_3)$alkyl; and X is (a) a $(C_3-C_6)$alkyl, a $(C_3-C_6)$alkoxy, a $(C_3-C_7)$carboxyalkyl, a $(C_1-C_4)$-alkoxycarbonyl$(C_3-C_6)$alkyl, a $(C_3-C_7)$carboxyalkoxy or a $(C_1-C_4)$alkoxycarbonyl $(C_3-C_6)$alkoxy; (b) a radical selected from a $(C_3-C_7)$cycloalkyl, $(C_3-C_7)$cycloalkoxy, $(C_3-C_7)$cycloalkylmethyl, $(C_3-C_7)$cycloalkylamino and cyclohexenyl, it being possible for said radical to be substituted by a halogen, hydroxyl, $(C_1-C_4)$alkoxy, carboxyl, $(C_1-C_4)$alkoxycarbonyl, amino or mono- or di-$(C_1-C_4)$alkylamino; or (c) a group selected from a phenyl, phenoxy, phenylamino, N-$(C_1-C_3)$alkylphenylamino, phenylmethyl, phenylethyl, phenylcarbonyl, phenylthio, phenylsulfonyl, phenylsulfinyl and styryl, it being possible for said group to be monosubstituted or polysubstituted on the phenyl group by a halogen, $CF_3$, $(C_1-C_4)$alkyl, $(C_1-C_4)$alkoxy, cyano, amino, mono- or di-$(C_1-C_4)$alkylamino, $(C_1-C_4)$acylamino, carboxyl, $(C_1-C_4)$-alkoxycarbonyl, aminocarbonyl, mono- or di-$(C_1-C_4)$-alkyl-aminocarbonyl, amino$(C_1-C_4)$alkyl, hydroxy$(C_1-C_4)$alkyl or halogeno$(C_1-C_4)$alkyl, as well as the salts and solvates thereof and the quaternary ammonium salts thereof; to a process for their preparation and to pharmaceutical compositions containing them.

These compounds have a neurotrophic and neuroprotective activity.

51 Claims, No Drawings

4-ARYL-1-PHENYLALKYL-1,2,3,6-TETRAHYDROPYRIDINES HAVING NEUROTROPHIC AND NEUROPROTECTIVE ACTIVITY

This application is a 371 of PCT/FR96/00995 filed Jun. 26, 1996.

The present invention relates to novel 4-substituted 1-phenylalkyl-1,2,3,6-tetrahydropyridines with a neurotrophic and neuroprotective activity, to a process for their preparation and to pharmaceutical compositions in which they are present.

EP-0 458 696 describes the use of a 1-(2-naphthylethyl)-4-(3-trifluoromethylphenyl)-1,2,3,6-tetrahydropyridine for the preparation of drugs for the treatment of cerebral and neuronal disorders.

WO 93/11107 describes piperidines and tetrahydropyridines with a protective activity on the damage caused by hypoxic/ischemic states.

It has now been found that certain phenylalkyl-1,2,3,6-tetrahydropyridines substituted by a phenyl or pyridyl group exert a neurotrophic action on the nervous system which is similar to the action of nerve growth factor (NGF), and can restore function to cells which are damaged or exhibit anomalies in their physiological functions.

According to one of its features, the present invention therefore relates to the compounds of formula (I):

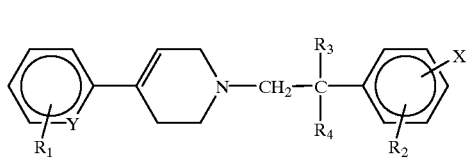

in which
Y is —CH— or —N—;
$R_1$ is hydrogen, a halogen or a $CF_3$, $(C_3-C_4)$alkyl or $(C_{1-C4})$ alkoxy group;
$R_2$ is hydrogen, a halogen, a hydroxyl or a $CF_3$, $(C_3-C_4)$ alkyl or $(C_1-C_4)$alkoxy group;
$R_3$ and $R_4$ are each hydrogen or a $(C_1-C_3)$alkyl; and
X is
(a) a $(C_3-C_6)$alkyl, a $(C_3-C_6)$alkoxy, a $(C_3-C_7)$ carboxyalkyl, a $(C_1-C_4)$alkoxycarbonyl$(C_3-C_6)$alkyl, a $(C_3-C_7)$carboxyalkoxy or a $(C_1-C_4)$alkoxycarbonyl $(C_3-C_6)$alkoxy;
(b) a radical selected from a $(C_3-C_7)$cycloalkyl, $(C_3-C_7)$ cycloalkoxy, $(C_3-C_7)$cycloalkylmethyl, $(C_3-C_7)$ cycloalkylamino and cyclohexenyl, it being possible for said radical to be substituted by a halogen, hydroxyl, $(C_1-C_4)$alkoxy, carboxyl, $(C_1-C_4)$ alkoxycarbonyl, amino or mono- or di-$(C_1-C_4)$ alkylamino; or
(c) a group selected from a phenyl, phenoxy, phenylamino, N-$(C_1-C_3)$alkylphenylamino, phenylmethyl, phenylethyl, phenylcarbonyl, phenylthio, phenylsulfonyl, phenylsulfinyl and styryl, it being possible for said group to be monosubstituted or polysubstituted on the phenyl group by a halogen, $CF_3$, $(C_1-C_4)$alkyl, $(C_1-C_4)$alkoxy, cyano, amino, mono- or di-$(C_1-C_4)$alkylamino, $(C_1-C_4)$acylamino, carboxyl, $(C_1-C_4)$alkoxycarbonyl, aminocarbonyl, mono- or di-$(C_1-C_4)$alkylaminocarbonyl, amino $(C_1-C_4)$alkyl, hydroxy$(C_1-C_4)$alkyl or halogeno $(C_1-C_4)$alkyl, the salts and solvates thereof and the quaternary ammonium salts thereof.

In the present description the term "$(C_1-C_3)$alkyl" denotes methyl, ethyl, n-propyl and i-propyl groups.

The term "$(C_1-C_4)$alkyl" denotes methyl, ethyl, n-propyl, i-propyl, n-butyl, i-butyl, s-butyl and t-butyl groups.

The term "$(C_3-C_6)$alkyl" denotes a saturated or unsaturated hydrocarbon radical containing from 3 to 6 carbon atoms, such as, for example, n-propyl, i-propyl, n-butyl, i-butyl, s-butyl, t-butyl, n-pentyl, i-pentyl, neopentyl, t-pentyl, n-hexyl, i-hexyl etc.

The term "alkoxy" denotes a hydroxyl group substituted by an alkyl, alkenyl or alkynyl group.

If X is a phenyl group, the nomenclature used for the biphenyl radical conforms to the IUPAC rules, i.e. the numbering of the positions of the two rings is as follows:

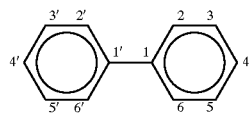

and the radicals having this structure are named as follows:

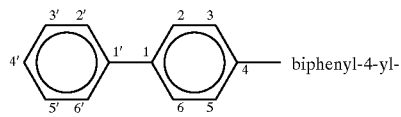 biphenyl-4-yl-

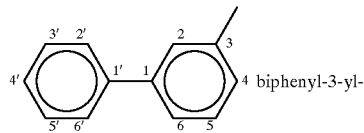 biphenyl-3-yl-

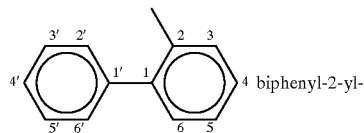 biphenyl-2-yl-

The compounds of formula (I) in which X is in the 4-position of the phenyl group, and the salts thereof, especially those which are pharmaceutically acceptable, the solvates thereof and the quaternary ammonium salts thereof, are particularly advantageous compounds.

One preferred group of compounds among those of formula (I) in which X is a group (c) is represented by the compounds in which the phenyl is substituted by 1 to 3 halogen, 1 to 3 $CF_3$, 1 to 3 $(C_1-C_4)$alkyl, 1 to 3 $(C_1-C_4)$ alkoxy, 1 to 3 cyano, 1 to 3 amino, 1 to 3 mono- or di-$(C_1-C_4)$alkylamino, 1 to 3 $(C_1-C_4)$acylamino, 1 to 3 carboxyl, 1 to 3 $(C_1-C_4)$alkoxycarbonyl, 1 to 3 aminocarbonyl, 1 to 3 mono- or di-$(C_1-C_4)$ alkylaminocarbonyl, 1 to 3 amino$(C_1-C_4)$alkyl, 1 to 3 hydroxy$(C_1-C_4)$alkyl or 1 to 3 halogeno$(C_1-C_4)$alkyl.

Another preferred group consists of the compounds of formula (I) in which Y is a group —CH— and $R_1$ is $CF_3$.

Another preferred group consists of the compounds of formula (I) in which Y is a nitrogen atom and $R_1$ is a chlorine atom.

The following are particularly advantageous compounds according to the present invention:

1-[2-(4-isobutylphenyl)propyl]-4-(3-trifluoromethylphenyl)-1,2,3,6-tetrahydropyridine;

1-[(2S)-2-(4-isobutylphenyl)propyl]-4-(3-trifluoromethylphenyl)-1,2,3,6-tetrahydropyridine;

1-[(2R)-2-(4-isobutylphenyl)propyl]-4-(3-trifluoromethylphenyl)-1,2,3,6-tetrahydropyridine;

1-[2-(4-isobutylphenyl)ethyl]-4-(3-trifluoromethylphenyl)-1,2,3,6-tetrahydropyridine;
1-[2-(4-tert-butylphenyl)ethyl]-4-(3-trifluoromethylphenyl)-1,2,3,6-tetrahydropyridine;
1-[2-(4-isobutylphenyl)-2-methylpropyl]-4-(3-trifluoro-methylphenyl)-1,2,3,6-tetrahydropyridine;
1-[2-(4-isopropylphenyl)ethyl]-4-(3-trifluoromethylphenyl)-1,2,3,6-tetrahydropyridine;
1-[2-(3'-chlorobiphenyl-4-yl)ethyl]-4-(3-trifluoro-methylphenyl)-1,2,3,6-tetrahydropyridine;
1-[2-(2'-chlorobiphenyl-4-yl)ethyl]-4-(3-trifluoro-methylphenyl)-1,2,3,6-tetrahydropyridine;
1-[2-(4'-chlorobiphenyl-4-yl)ethyl]-4-(3-trifluoro-methylphenyl)-1,2,3,6-tetrahydropyridine;
1-[2-(4'-fluorobiphenyl-4-yl)ethyl]-4-(3-trifluoro-methylphenyl)-1,2,3,6-tetrahydropyridine;
1-[2-(3'-trifluoromethylbiphenyl-4-yl)ethyl]-4-(3-tri-fluoromethylphenyl)-1,2,3,6-tetrahydropyridine;
1-[2-(4-cyclohexylphenyl)ethyl]-4-(3-trifluoromethylphenyl)-1,2,3,6-tetrahydropyridine;
1-[2-(biphenyl-4-yl)-2-ethyl]-4-(4-fluorophenyl)-1,2,3,6-tetrahydropyridine;
1-[2-(biphenyl-4-yl)-2-methylpropyl]-4-(3-trifluoro-methylphenyl)-1,2,3,6-tetrahydropyridine;
1-[2-(4-phenoxyphenyl)-2-ethyl]-4-(3-trifluoromethylphenyl)-1,2,3,6-tetrahydropyridine;
1-[2-(4-benzylphenyl)-2-ethyl]-4-(3-trifluoromethylphenyl)-1,2,3,6-tetrahydropyridine;
1-[2-(4-n-butylphenyl)ethyl]-4-(3-trifluoromethylphenyl)-1,2,3,6-tetrahydropyridine;
1-[2-(biphenyl-4-yl)ethyl]-4-(3-trifluoromethylphenyl)-1,2,3,6-tetrahydropyridine;
1-[2-(4-n-butoxyphenyl)ethyl]-4-(3-trifluoromethylphenyl)-1,2,3,6-tetrahydropyridine;
1-[2-(4-(3-ethoxycarbonylpropoxy)phenyl)ethyl]-4-(3-trifluoromethylphenyl)-1,2,3,6-tetrahydropyridine;
1-[2-(biphenyl-4-yl)ethyl]-4-(6-chloropyrid-2-yl)-1,2,3,6-tetrahydropyridine;
1-[2-(2,3'-dichlorobiphenyl-4-yl)ethyl]-4-(3-trifluoro-methylphenyl)-1,2,3,6-tetrahydropyridine;
1-[2-(3-chlorobiphenyl-4-yl)ethyl]-4-(3-trifluoro-methylphenyl)-1,2,3,6-tetrahydropyridine;
1-[2-(3',5'-dichlorobiphenyl-4-yl)ethyl]-4-(3-tri-fluoromethylphenyl)-1,2,3,6-tetrahydropyridine;
1-[2-(2',4'-dichlorobiphenyl-4-yl)ethyl]-4-(3-tri-fluoromethylphenyl)-1,2,3,6-tetrahydropyridine;
1-[2-(2-chlorobiphenyl-4-yl)ethyl]-4-(3-trifluoro-methylphenyl)-1,2,3,6-tetrahydropyridine;
1-[2-(3'-chlorobiphenyl-4-yl)-2-methylpropyl]-4-(3-tri-fluoromethylphenyl)-1,2,3,6-tetrahydropyridine;
1-[2-(2-fluorobiphenyl-4-yl)propyl]-4-(3-trifluoro-methylphenyl)-1,2,3,6-tetrahydropyridine;
1-[2-(4-methoxybiphenyl-3-yl)ethyl]-4-(3-trifluoro-methylphenyl)-1,2,3,6-tetrahydropyridine;
1-[2-(4'-methoxybiphenyl-4-yl)ethyl]-4-(3-trifluoro-methylphenyl)-1,2,3,6-tetrahydropyridine;
1-[2-(4'-hydroxybiphenyl-4-yl)ethyl]-4-(3-trifluoro-methylphenyl)-1,2,3,6-tetrahydropyridine;
1-[2-(4'-ethoxycarbonylbutoxybiphenyl-4-yl)ethyl]-4-(3-trifluoromethylphenyl)-1,2,3,6-tetrahydropyridine;
1-[2-(biphenyl-3-yl)ethyl]-4-(3-trifluoromethylphenyl)-1,2,3,6-tetrahydropyridine;
1-[2-(3'-chloro-4'-fluorobiphenyl-4-yl)ethyl]-4-(3-tri-fluoromethylphenyl)-1,2,3,6-tetrahydropyridine;
1-[2-(2'-trifluoromethylbiphenyl-4-yl)ethyl]-4-(3-tri-fluoromethylphenyl)-1,2,3,6-tetrahydropyridine;
1-[2-(3,4-diisobutylphenyl)ethyl]-4-(3-trifluoromethylphenyl)-1,2,3,6-tetrahydropyridine;
1-[2-(3,4-dipropylphenyl)ethyl]-4-(3-trifluoromethylphenyl)-1,2,3,6-tetrahydropyridine;
1-[2-(4-cyclohexylphenyl)ethyl]-4-(6-chloropyrid-2-yl)-1,2,3,6-tetrahydropyridine;
1-[2-(4-isobutylphenyl)propyl]-4-(6-chloropyrid-2-yl)-1,2,3,6-tetrahydropyridine;
and the salts thereof.

According to another of its features, the present invention relates to a process for the preparation of the compounds of formula (I), the salts or solvates thereof and the quaternary ammonium salts thereof, wherein (a) an aryl-1,2,3,6-tetrahydropyridine of formula (II):

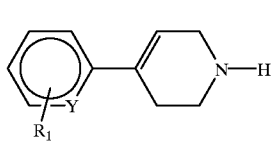

in which Y and $R_1$ are as defined above, is reacted with a compound of formula (III):

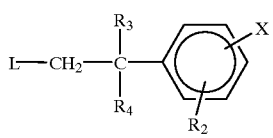

in which $R_2$, $R_3$, $R_4$ and X are as defined above and L is a leaving group such as, for example, a chlorine, bromine or iodine atom or the methanesulfonyloxy, p-toluenesulfonyloxy or trifluoromethylsulfonyloxy group; and (b) the resulting compound of formula (I) is isolated and optionally converted to a salt or solvate thereof or a quaternary ammonium salt thereof.

The reaction is carried out in an organic solvent at a temperature between room temperature and the reflux temperature of the solvent used.

The organic solvent used is preferably an aliphatic alcohol having from 1 to 6 carbon atoms, such as methanol, ethanol, isopropanol, n-butanol or n-pentanol, but it is also possible to use other solvents such as hexane, dimethylformamide, dimethylsulfoxide, sulfolane, acetonitrile, pyridine and the like.

The reaction is advantageously carried out in the presence of a basic agent such as an alkali metal carbonate or triethylamine, especially in the case where L is a halogen atom.

The reaction temperature can vary between room temperature (about 20° C.) and the reflux temperature, the reaction times varying accordingly. In general, after 6 to 12 hours of refluxing, the reaction has ended and the final product obtained can be isolated by the conventional techniques in the form of the free base or a salt thereof, the free base optionally being converted to a salt thereof by simple salification in an organic solvent such as an alcohol, preferably ethanol or isopropanol, an ether like 1,2-dimethoxyethane, ethyl acetate, acetone or a hydrocarbon like hexane.

Alternatively the compounds of formula (I) in which Y is —CH—, the salts or solvates thereof and the quaternary ammonium salts thereof can be prepared by a process wherein (a) the compound of formula (IV):

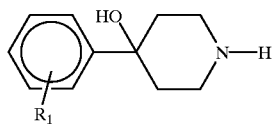

in which $R_1$ is as defined above, is reacted with a functional derivative of the acid of formula (V):

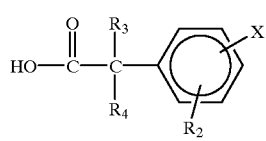

in which $R_2$, $R_3$, $R_4$ and X are as defined above,
(b) the carbonyl group of the compound of formula (VI):

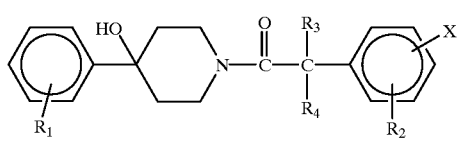

is reduced,
(c) the intermediate piperidinol of formula (VII):

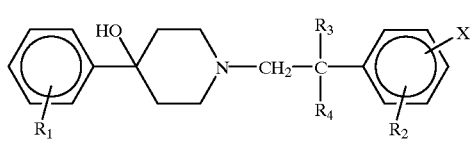

is dehydrated and
(d) the resulting compound of formula (I) is isolated and optionally converted to a salt or solvate thereof or a quaternary ammonium salt thereof.

The reaction of step (a) can conveniently be carried out in an organic solvent at a temperature between −10° C. and the reflux temperature of the reaction mixture.

Appropriate functional derivatives of the acid of formula (V) which can be used are the free acid (optionally activated with BOP, for example), the anhydride, a mixed anhydride, an active ester or an acid halide, preferably the bromide. Of the active esters the p-nitrophenyl ester is particularly preferred, but the methoxyphenyl, trityl, benzhydryl and similar esters are also suitable.

The reaction temperature can vary between −10° C. and the reflux temperature, but the reaction is generally carried out at room temperature or at 30–50° C. It can be preferable to carry out the reaction in the cold if it is exothermic, as in the case where the chloride is used as the functional derivative of the acid of formula (V).

The reaction solvent used is preferably a halogenated solvent such as methylene chloride, dichloroethane, 1,1,1-trichloroethane, chloroform or the like, or an alcohol such as methanol or ethanol, but it is also possible to employ other organic solvents compatible with the reactants used, for example dioxane, tetrahydrofuran or a hydrocarbon such as hexane.

The reaction can conveniently be carried out in the presence of a proton acceptor, for example an alkali metal carbonate or a tertiary amine.

The reduction of step (b) can conveniently be carried out with appropriate reducing agents such as borane complexes, for example borane/dimethyl sulfide, aluminum hydrides or a complex lithium aluminum hydride, in an inert organic solvent at a temperature between 0° C. and the reflux temperature of the reaction mixture, using the customary techniques.

"Inert organic solvent" is understood as meaning a solvent which does not interfere with the reaction. Examples of such solvents are ethers like diethyl ether, tetrahydrofuran, dioxane or 1,2-dimethoxyethane.

In a preferred mode of carrying out the invention, the reaction is performed with borane/dimethyl sulfide used in excess relative to the initial compound (VI), at the reflux temperature, optionally under an inert atmosphere. The reduction has normally ended after a few hours.

The dehydration of step (c) is easy to carry out, for example using an acetic acid/sulfuric acid mixture at a temperature between room temperature and the reflux temperature of the solvent used.

In a preferred method, the reaction of step (c) is carried out in an acetic acid/sulfuric acid mixture in a volume ratio of 1/3, the reaction mixture being heated at a temperature of about 110° C. for 1–3 hours.

The desired compound is isolated by the conventional techniques in the form of the free base or a salt thereof. The free base can be converted to a salt thereof by simple salification in an organic solvent such as an alcohol, preferably ethanol or isopropanol, an ether like 1,2-dimethoxyethane, ethyl acetate, acetone or a hydrocarbon like hexane.

The compound of formula (I) obtained is isolated by the customary techniques and optionally converted to an acid addition salt thereof or, if there is an acid group present, the amphoteric character of the compound enables the salts to be separated with either acids or bases.

The compounds of formulae (VI) and (VII), which can be jointly represented by formula (i):

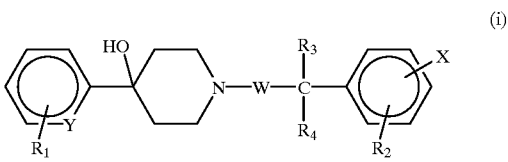

in which $R_1$, $R_2$, $R_3$, $R_4$, X and Y are as defined above and W is a methylene group or a carbonyl group, said compounds being key intermediates in the synthesis of the compounds of formula (I), are novel compounds and constitute a further subject of the present invention.

If salts of the compound of formula (I) are prepared for administration as drugs, the acids or bases employed must be pharmaceutically acceptable; if salts of the compound of formula (I) are prepared for another purpose, for example to improve the purification of the product or to facilitate analytical assays, any acid or base can then be used.

Examples of the salts with pharmaceutically acceptable bases are those with alkali or alkaline earth metals such as sodium, potassium, calcium or magnesium, and those with organic bases such as amines, basic amino acids (lysine, arginine, histidine), trometamol, N-methylglutamine, etc.

Examples of the salts with pharmaceutically acceptable acids are those with mineral acids, such as the hydrochloride, hydrobromide, borate, phosphate, sulfate, hydrogensulfate and hydrogenphosphate, and those with organic acids, such as the citrate, benzoate, ascorbate, methylsulfate, naphthalene-2-sulfonate, picrate, fumarate, maleate, malonate, oxalate, succinate, acetate, tartrate, mesylate, tosylate, isethionate, α-ketoglutarate, α-glycerophosphate, glucose-1-phosphate, etc.

The starting amines of formula (II) in which Y is —CH— are known compounds or can be prepared by processes analogous to those used to prepare known compounds.

The starting amines of formula (II) in which Y is N can be prepared by reacting the appropriate 2-halogenopyridine of formula (p):

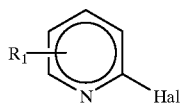

(p)

with a 1,2,3,6-tetrahydropyridine of formula (q):

(q)

in which P° is a protecting group, such as the benzyl group, and Z is a substituent which permits nucleophilic substitution of the halogen on the pyridine. Examples of such substituents are trialkylstannanes, such as tributylstannane, or Grignard compounds.

The 1,2,3,6-tetrahydropyridine is then deprotected by cleavage of the protecting group under suitable conditions.

The amines of formula (II') below:

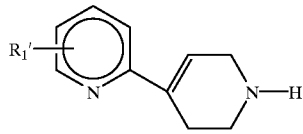

(II')

in which $R_1'$ is a halogen, $CF_3$, $(C_3-C_4)$alkyl or $(C_1-C_4)$alkoxy, and the salts thereof, are novel compounds and constitute a further subject of the present invention.

The compounds of formula (III) can be prepared
either by reducing the acids of formula (V) to the alcohol
and converting the hydroxyl group to a leaving group;
or, to prepare a compound of formula (III) in which $R_3 = R_4 = H$, by reacting the appropriate benzene of formula (r):

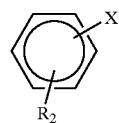

(r)

in which $R_2$ and X are as defined above, with an acyl halide of the formula L—$CH_2$—CO—Hal, in the presence of a Lewis acid, according to the well-known Friedel-Crafts reaction, and reducing the resulting ketone of formula (s):

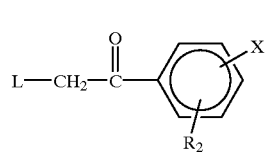

(s)

by the procedures widely described in the literature.

The acids of formula (V) are generally compounds which are described in the literature. A large number of these compounds are generally described as antiinflammatories, examples being hexaprofen, tetriprofen, alclofenac, butiprofen, mexoprofen, ibufenac, ibuprofen, flurbiprofen, phenoprofen, fenclofenac, etc.

The starting materials (III) and (V) in which X is an optionally substituted phenyl group can also be prepared by an original process, Suzuki's reaction being carried out in an aqueous medium in a novel process which constitutes a further subject of the present invention.

Thus, according to another of its features, the present invention relates to a process for the preparation of biphenylyl derivatives by means of a condensation reaction between phenyl derivatives substituted by a leaving group and benzeneboronic acids in the presence of a catalyst, a strong base and a phase transfer agent.

The present invention therefore also relates to a process for the preparation of the compounds of formula (t) below:

(t)

in which the benzene can optionally be substituted and X' is a phenyl optionally monosubstituted or polysubstituted by a halogen, $CF_3$, $(C_1-C_4)$alkyl, $(C_1-C_4)$alkoxy, cyano, amino, mono- or di-$(C_1-C_4)$alkylamino, $(C_1-C_4)$acylamino, carboxyl, $(C_1-C_4)$alkoxycarbonyl, aminocarbonyl, mono- or di-$(C_1-C_4)$alkylaminocarbonyl, amino$(C_1-C_4)$alkyl, hydroxy$(C_1-C_4)$alkyl or halogeno$(C_1-C_4)$alkyl, said process consisting in reacting a compound of formula (w):

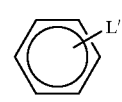

(w)

in which the benzene can optionally be substituted and L' is a leaving group as defined above for L, with a benzeneboronic acid of the formula X'—$B(OH)_2$, in which X' is as defined above, in the presence of a palladium salt, a strong base and a phase transfer agent, in an aqueous medium.

More particularly, and according to an advantageous feature, the present invention relates to a process for the preparation of the compounds of formula (t'):

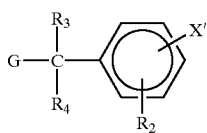

(t')

in which $R_2$, $R_3$, $R_4$ and X' are as defined above and G is a carboxyl group or a group L—$CH_2$—, in which L is a leaving group as defined above, which process consists in reacting a compound of formula (w'):

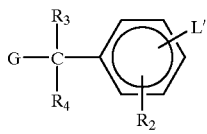

(w')

in which $R_2$, $R_3$, $R_4$, G and L' are as defined above, with a benzeneboronic acid of the formula X'—$B(OH)_2$, in which X' is as defined above, in the presence of a palladium salt, a strong base and a phase transfer agent, in an aqueous medium.

Preferred leaving groups L' are bromine and the trifluoromethylsulfonyloxy group.

Palladium acetate is a preferred palladium salt.

Examples of strong bases which can be used are alkali metal hydroxides or carbonates such as sodium hydroxide or carbonate or potassium hydroxide or carbonate.

Phase transfer agents which can be used are tetraalkylammonium halides, tetrabutylammonium bromide being particularly advantageous.

The reaction is advantageously carried out by heating the mixture to between 30° C. and the reflux point, especially to between 50° C. and 80° C. and preferably to about 70° C.

The reaction finishes rapidly, normally in a few hours, depending on the operating temperature.

The products of formula (t') and the acids of the formula X'—$B(OH)_2$ are known in the literature or can be prepared by methods analogous to those used for known compounds. Synthesis Examples are nevertheless included in the experimental section of the present description.

The activity of the compounds of formula (I) on the nervous system was demonstrated in in vitro and in vivo studies using the methods described in EP-0 458 696 and, for evaluation of the neuronal survival, by means of an in vitro survival test conducted using neurons isolated from the dissected septal region of rat embryos.

More particularly, the septal region of 17- to 18-day-old rat embryos was removed under a dissecting microscope under sterile conditions and then dissociated in a trypsin/EDTA medium. The cell suspension was placed in a culture flask in a DME/Ham's F12 (v:v) medium (Dulbecco Modified Eagle's Medium/Ham's F12 Nutrient Mixture—R. G. Ham, Proc. Nat. Sci., 1965, 53:288) containing 5% calf serum and 5% horse serum, and maintained at 37° C. for 90 minutes. This treatment makes it possible to eliminate the non-neuronal cells.

The neuroblasts are then inoculated into the wells of a titer plate at a rate of $17 \times 10^4$ cells/$cm^2$, in a non-serum culture medium consisting of DME/Ham's F12 containing selenium (30 nM) and transferrin (1.25 μM). Each well has first been treated with poly-L-lysine. The inoculated plates are placed in an incubator in the oven (37° C.; 5% $CO_2$).

The test compounds are dissolved in DMSO and diluted with the culture medium as required.

The neuroblasts are kept for 4 days in plates containing the test compound or the corresponding solvent, without changing the medium.

After 4 days the medium is replaced with a tetrazolium salt dissolved in the culture medium (0.15 mg/ml). The cells are then placed in the oven at 37° C. for 4 hours. The mitochondrial succinate dehydrogenases of the live cells reduce the tetrazolium salt to formazan blue, the optical density of which is measured at 540 nm after dissolution in DMSO; said density has a linear correlation with the number of live cells (Manthorpe et al., Dev. Brain Res., 1988, 25:191–198).

The difference between the groups containing the test compounds and the controls was evaluated by statistical analysis using the two-tailed Dunnett t-test.

In said test the compounds of formula (I) proved as active as or more active than the compounds described in EP-0 458 696, the efficacy of some compounds of formula (I) in respect of neuronal survival being double that of compound A described in EP-0 458 696.

By virtue of this potent neuroprotective activity and their low toxicity, which is compatible with their use as drugs, the compounds of formula (I), the pharmaceutically acceptable addition salts thereof, the solvates thereof and the quaternary ammonium salts thereof can be used for the preparation of pharmaceutical compositions indicated in the treatment and/or prophylaxis of all diseases which involve neuronal degeneration. More particularly, the compounds of the invention can be used, either by themselves or in co-administration or association with other active principles acting on the CNS, for example selective M1 cholinomimetics, NMDA antagonists or nootropics such as piracetam, especially in the following indications: memory disorders, vascular dementia, postencephalitic disorders, postapoplectic disorders, posttraumatic syndromes due to a cranial traumatism, disorders deriving from cerebral anoxia, Alzheimer's disease, senile dementia, subcortical dementia such as Huntington's chorea and Parkinson's disease, dementia caused by AIDS, neuropathy deriving from morbidity or damage to the sympathetic or sensory nerves, brain diseases such as cerebral edema, spinocerebellar degenerations and motor neuron degenerations such as, for example, amyotrophic lateral sclerosis.

According to another feature, the invention relates to a method of treating the above-mentioned complaints which consists in administering to a patient in need a therapeutically effective amount of a compound according to the invention, as such or mixed with conventional pharmaceutical carriers.

The compounds of the invention can conveniently be administered orally, parenterally, sublingually or transdermally. The amount of active principle to be administered in the treatment of cerebral and neuronal disorders by the method of the present invention depends on the nature and severity of the complaints to be treated and on the weight of the patients. Nevertheless the preferred unit doses will generally comprise from 0.5 to 700 mg of product, advantageously from 2 to 300 mg and preferably from 5 to 150 mg, for example between 5 and 50 mg, namely 1, 2, 5, 10, 15, 20, 25, 30, 40 or 50 mg. These unit doses will normally be administered one or more times a day, for example 2, 3, 4 or 5 times a day and preferably one to three times a day, the overall human dose varying between 1 and 1400 mg per day and advantageously between 2 and 900 mg per day, for example from 3 to 500 mg and more conveniently from 10 to 300 mg per day.

In the pharmaceutical compositions of the present invention for oral, sublingual, subcutaneous, intramuscular, intravenous, transdermal or rectal administration, the active principle can be administered to animals and humans in unit forms of administration, either as such, for example in lyophilized form, or mixed with conventional pharmaceutical carriers, for the treatment of the above-mentioned complaints. The appropriate unit forms of administration include oral forms such as tablets, which may be divisible, gelatin capsules, powders, granules and solutions or suspensions to be taken orally, sublingual and buccal forms of administration, subcutaneous, intramuscular or intravenous forms of administration, local forms of administration and rectal forms of administration.

When a solid composition in the form of tablets is prepared, the main active ingredient is mixed with a pharmaceutical vehicle such as gelatin, starch, lactose, magnesium stearate, talc, gum arabic or the like. The tablets can be coated with sucrose or other appropriate substances or else they can be treated so as to have a prolonged or delayed activity and so as to release a predetermined amount of active principle continuously.

A preparation in the form of gelatin capsules is obtained by mixing the active ingredient with a diluent and pouring the mixture obtained into soft or hard gelatin capsules.

A preparation in the form of a syrup or elixir can contain the active ingredient together with a sweetener, which is preferably calorie-free, methylparaben and propylparaben as antiseptics, a flavoring and an appropriate color.

The water-dispersible granules or powders can contain the active ingredient mixed with dispersants or wetting agents or with suspending agents such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral administration is effected using aqueous suspensions, saline solutions or sterile and injectable solutions which contain pharmacologically compatible dispersants and/or wetting agents, for example propylene glycol or butylene glycol.

The active principle can also be formulated as microcapsules, with one or more carriers or additives if appropriate.

In the pharmaceutical compositions according to the present invention, the active principle can also be in the form of an inclusion complex in cyclodextrins or ethers or esters thereof.

The Examples which follow illustrate the invention more clearly without however implying a limitation.

PREPARATION 1
2-Trifluoromethylbenzeneboronic acid 1.36 ml (0.01 mmol) of 2-bromotrifluoromethylbenzene and 10 ml of anhydrous ethyl ether are mixed under an argon atmosphere. The mixture is cooled to 0° C., 7 ml of BuLi (1.6 M solution in hexane) are added and the mixture is left at a temperature of 0° C. for 2 hours. It is then transferred to a solution of 3 ml of triisopropylborate (0.0125 mol) and 15 ml of anhydrous THF at −78° C. under an argon atmosphere.

The mixture is left at −78° C. for 3 hours and then at room temperature overnight. It is poured into 1 N aqueous hydrochloric acid solution and extracted with ethyl ether, the organic phase is dried over sodium sulfate and the solvent is evaporated off under reduced pressure.

The residue is treated with hexane and the precipitate formed is filtered off to give 0.7 g of the title compound. M.p.=140–143° C.

PREPARATION 2
3-Chlorobenzeneboronic acid

The title compound is obtained by following the procedure described in Preparation 1 but using 3-bromochlorobenzene instead of 2-bromotrifluoromethylbenzene. M.p.=176–178° C.

PREPARATION 3
(2-Chloro-4-methoxyphenyl)acetic acid
3i/2-Chloro-4-methoxyacetophenone 14.3 g (0.11 mol) of 3-chloroanisole are added at 0° C. to a mixture of 9.3 ml (0.13 mol) of acetyl chloride and 350 ml of methylene chloride. The mixture is stirred for 1 hour and then, with the temperature maintained at 0° C., 24 g (0.18 mol) of aluminum chloride are added and the reaction is allowed to proceed at this temperature for 2 hours. 20 ml of 1 N hydrochloric acid solution and 20 ml of water are then added. The two phases are separated, the organic phase is washed with water, dried over sodium sulfate and filtered and the solvent is evaporated off under reduced pressure. The crude product is purified by chromatography on a silica gel column using an 8/2 cyclohexane/ethyl acetate mixture as the eluent to give the title compound.
3ii/4-(2-Chloro-4-methoxybenzylthiocarbonyl)morpholine A mixture of 5.52 g (0.03 mol) of the product of the previous step, 7.1 ml of morpholine and 1.15 g of sulfur is heated at 130° C. for 4 hours. 1 N hydrochloric acid solution is then added and the mixture is extracted with ethyl acetate. The two phases are separated, the organic phase is dried over sodium sulfate and the solvent is evaporated off under reduced pressure. The crude product is treated with 2.5 ml of ethyl acetate and the precipitate formed is filtered off to give the title compound. M.p.=100–102° C.
3iii/(2-Chloro-4-methoxyphenyl)acetic acid A mixture of 6.6 g of the product of the previous step, 35 ml of ethanol and a solution of 3 g of sodium hydroxide in 55 ml of water is refluxed for 8 hours. It is washed with ethyl ether and the aqueous solution is acidified with 1 N hydrochloric acid and extracted with ethyl ether. The organic phase is dried over sodium sulfate and filtered and the solvent is evaporated off under reduced pressure to give the title compound. M.p.=115–117° C.

PREPARATION 4
(2-Chloro-4-hydroxyphenyl)acetic acid

A solution of 1.6 g (8 mmol) of (2-chloro-4-methoxyphenyl)acetic acid, prepared according to Preparation 3, in 13 ml of hydrobromic acid (in 48% aqueous solution) is refluxed for two hours. After cooling, ammonium hydroxide is added until the pH is basic, and the mixture is extracted with methylene chloride. The water is evaporated from the aqueous phase and the residue is washed several times with ethanol to give the title compound.

EXAMPLE 1
1-[2-(4-Isobutylphenyl)propyl]-4-(3-trifluoromethyl-phenyl)-1,2,3,6-tetrahydropyridine hydrochloride 1a/Ethyl 2-(4-isobutylphenyl)propionate Gaseous hydrochloric acid is bubbled for one hour into a solution of 50 g (0.242 mol) of 2-(4-isobutylphenyl)propionic acid in 700 ml of absolute ethanol and the mixture is then refluxed for two hours. The solvent is evaporated off and the residue is taken up with ethyl acetate. The mixture is washed with aqueous sodium bicarbonate solution and dried over sodium sulfate and the solvent is evaporated off under reduced pressure to give the title compound.
1b/2-(4-Isobutylphenyl)propyl alcohol A solution of 59 g (0.25 mol) of the compound of the previous step in 450 ml of ethyl ether is added under nitrogen to a suspension of 9.55 g of lithium aluminum hydride in 50 ml of ethyl ether, the temperature being maintained at 20° C. The reaction mixture is stirred at room temperature for 2 hours and a solution of 60 ml of 95% ethanol and 60 ml of water is then added, with extreme caution, to destroy the unreacted hydride. The salts formed are filtered off and the filtrate is evaporated under reduced pressure to give the title compound.

1c/2-(4-Isobutylphenyl)propyl methanesulfonate

A mixture of 15.5 g (0.08 mol) of the compound of the previous step, 100 ml of methylene chloride and 24.2 g (0.1774 mol) of triethylamine is cooled to 0–5° C. and a solution of 12.9 g (0.1774 mol) of mesyl chloride in 10 ml of methylene chloride is added. The mixture is stirred at room temperature for 5 hours. The solution is then washed with 1 N hydrochloric acid solution, with water, with aqueous sodium bicarbonate solution and again with water. The organic phase is dried over sodium sulfate and the solvent is evaporated off under reduced pressure to give the title compound.

1d/1-[2-(4-Isobutylphenyl)propyl]-4-(3-trifluoro-methylphenyl)-1,2,3,6-tetrahydropyridine hydrochloride A mixture of 2.63 g (0.01 mol) of 4-(3-trifluoromethylphenyl)-1,2,3,6-tetrahydropyridine, 4.2 ml (0.03 mol) of triethylamine and 4 g (0.01 mol) of 2-(4-isobutylphenyl)-1-(methylsulfonyloxy)propane in 40 ml of isopropanol is refluxed overnight. The solvent is evaporated off under reduced pressure and the residue is purified by chromatography on a silica gel column using an 8/2 cyclohexane/ethyl acetate mixture as the eluent. The hydrochloride of the resulting oil is prepared with a solution of hydrochloric acid in ethyl ether. The precipitate obtained is filtered off and then crystallized from acetone. M.p.=190–192° C.

EXAMPLE 2

1-[(2S)-2-(4-Isobutylphenyl)propyl]-4-(3-trifluoro-methylphenyl)-1,2,3,6-tetrahydropyridine hydrochloride 2a/1-[(2S)-2-(4-Isobutylphenyl)propionyl]-4-hydroxy-4-(3-trifluoromethylphenyl)piperidine 2.06 g (0.01 mol) of (2S)-2-(4-isobutylphenyl)propionic acid, 35 ml of methylene chloride, 2.09 g (0.015 mol) of triethylamine, 2.45 g (0.01 mol) of 4-(3-trifluoromethylphenyl)-4-piperidinol and 4.42 g (0.01 mol) of BOP are mixed and the solution is stirred at room temperature for 1.5 hours. Ethyl acetate is then added and the mixture is washed with water, with 1 N hydrochloric acid, with water, with 1 N sodium hydroxide and with water. The organic phase is dried over sodium sulfate and the solvent is evaporated off under reduced pressure. The resulting crude oil is purified by chromatography on a silica gel column using a 9/1 ethyl acetate/cyclohexane mixture as the eluent. 3.3 g of the title product are isolated. M.p.=123–125° C. $[\alpha]_D^{20}$=–66.70° (c =1%, MeOH).

2b/1-[(2S)-2-(4-Isobutylphenyl)propyl]-4-hydroxy-4-(3-trifluoromethylphenyl)piperidine hydrochloride 3.0 g (0.0069 mol) of the product of the previous step in 30 ml of tetrahydrofuran are heated to the reflux point and 2.09 ml (0.02 mol) of borane/dimethyl sulfide in 20 ml of tetrahydrofuran are added. The mixture is refluxed for 4 hours, the solution is cooled to 10–15° C. and 15 ml of methanol are cautiously added dropwise. The mixture is stirred for 15 minutes at room temperature and then for 30 minutes under reflux. The solvent is evaporated off under reduced pressure and the residue is taken up with dilute aqueous ammonia solution. The mixture is extracted with ethyl acetate, the organic phase is washed with water and dried over sodium sulfate and the solvent is evaporated off under reduced pressure to give 3.0 g of a crude oil. The hydrochloride is prepared by treatment with a saturated solution of hydrochloric acid in isopropanol to give the title compound. M.p.=250–252° C. $[\alpha]_D^{20}$=+35.01° (c=1%, MeOH).

2c/1-[(2S)-2-(4-Isobutylphenyl)propyl]-4-(3-trifluoro-methylphenyl)-1,2,3,6-tetrahydropyridine hydrochloride 1.3 g (0.0023 mol) of the product of the previous step are dissolved in 10 ml of acetic acid, 3 ml of 96% sulfuric acid are added and the mixture is heated at 110° C. for 2 hours. It is poured into a water/ice mixture, concentrated sodium hydroxide solution is added and the resulting mixture is extracted with ethyl ether. The organic phase is washed with water and dried over sodium sulfate and the solvent is evaporated off under reduced pressure to give 1.25 g of a crude oil. The hydrochloride is prepared by treatment with a saturated solution of hydrochloric acid in isopropanol to give the title compound, which is crystallized from acetone. M.p.=223–225° C. $[\alpha]_D^{20}$=+46.8° (c=1%, MeOH).

EXAMPLE 3

1-[(2R)-2-(4-Isobutylphenyl)propyl]-4-(3-trifluoro-methylphenyl)-1,2,3,6-tetrahydropyridine hydrochloride 3a/1-[(2R)-2-(4-Isobutylphenyl)propionyl]-4-hydroxy-4-(3-trifluoromethylphenyl)piperidine The title product is obtained by following the procedure described in Example 2a but using (2R)-2-(4-isobutylphenyl)propionic acid. M.p.=122–124° C. $[\alpha]_D^{20}$=+68.7° (c=1%, MeOH).

3b/1-[(2R)-2-(4-Isobutylphenyl)propyl]-4-hydroxy-4-(3-trifluoromethylphenyl)piperidine hydrochloride The title product is obtained by following the procedure described in Example 2b using the compound of step 3a. M.p.=257–260° C. $[\alpha]_D^{20}$=–37.2° (c=1%, MeOH).

3c/1-[(2R)-2-(4-Isobutylphenyl)propyl]-4-(3-trifluoro-methylphenyl)-1,2,3,6-tetrahydropyridine hydrochloride The title product is obtained by following the procedure described in Example 2c using the compound of step 3b. M.p.=224–226° C. $[\alpha]_D^{20}$=–45.6° (c=1%, MeOH).

EXAMPLE 4

1-[2-(4-Isobutylphenyl)ethyl]-4-(3-trifluoromethyl-phenyl)-1,2,3,6-tetrahydropyridine hydrochloride 4a/1-Bromo-2-(4-isobutylphenyl)ethane A mixture of 5 g (0.0373 mol) of isobutylbenzene, 67 ml of methylene chloride and 9.86 g (0.0489 mol) of bromoacetyl bromide is cooled to 0–5° C. and 5.75 g (0.0431 mol) of aluminum trichloride are added. The mixture is stirred at 0–5° C. for one hour and then left at room temperature overnight. It is poured into a water/ice mixture and extracted with methylene chloride, the organic phase is dried over sodium sulfate and the solvent is evaporated off under reduced pressure. 4.6 g (0.018 mol) of the resulting oil are mixed with 9.7 ml (0.123 mol) of trifluoroacetic acid and 12.7 ml (0.0792 mol) of triethylsilane and the mixture is heated at 80° C. for 4 hours. Saturated aqueous sodium bicarbonate solution is then added until the pH is basic, the mixture is extracted with ethyl ether, the organic phase is dried over sodium sulfate and the solvent is evaporated off under reduced pressure. The resulting crude oil is purified by chromatography on a silica gel column using cyclohexane as the eluent to give the title compound. Thin layer chromatography (eluent: cyclohexane): Rf=0.5.

4b/1-[2-(4-Isobutylphenyl)ethyl]-4-(3-trifluoromethyl-phenyl)-1,2,3,6-tetrahydropyridine hydrochloride A mixture of 2.5 g (0.0095 mol) of 4-(3-trifluoro-methylphenyl)-1,2,3,6-tetrahydropyridine, 50 ml of butanol, 3.94 g (0.0285 mol) of anhydrous potassium carbonate chips and 2.3 g (0.0095 mol) of the product of the previous step is refluxed for 8 hours. The solvent is evaporated off under reduced pressure, the residue is taken up with ethyl acetate, the mixture is washed with water and dried over sodium sulfate and the solvent is evaporated off under reduced pressure. The hydrochloride of the resulting oil is prepared by treatment with a saturated solution of hydrochloric acid in isopropanol to give 2.4 g of the title compound, which is crystallized from isopropanol. M.p.= 242–246° C. Thin layer chromatography (eluent: cyclohexane/ethyl acetate=1/1): Rf=0.6.

EXAMPLE 5

1-[2-(4-Tert-butylphenyl)ethyl]-4-(3-trifluoromethyl-phenyl)-1,2,3,6-tetrahydropyridine hydrochloride 5a/1-Bromo-2-(4-tert-butylphenyl)ethane The title product is obtained by following the procedure described in Example 4a but using tert-butylbenzene instead of isobutylbenzene. Thin layer chromatography (eluent: cyclohexane): Rf=0.6.

5b/1-[2-(4-Tert-butylphenyl)ethyl]-4-(3-trifluoro-methylphenyl)-1,2,3,6-tetrahydropyridine hydrochloride The title compound is obtained by following the procedure described in Example 4b using the compound of step 5a. M.p.=261–265° C. Thin layer chromatography (eluent: cyclohexane/ethyl acetate=1/1): Rf=0.7.

EXAMPLE 6

1-[2-(4-Isobutylphenyl)-2-methylpropyl]-4-(3-trifluoro-methylphenyl)-1,2,3,6-tetrahydropyridine oxalate 6a/2-(4-Isobutylphenyl)-2-methylpropionic acid 5 g (0.0227 mol) of ethyl 2-(4-isobutylphenyl)propionate (Example 1a) are dissolved in 50 ml of DMF, and 1.6 g (0.025 mol) of sodium hydride are added in portions. After 30 minutes 3.2 ml (0.0375 mol) of methyl iodide are added. The mixture is stirred at room temperature for 2 hours, poured into a water/ice mixture and extracted with ethyl acetate, the extract is washed with water and dried over sodium sulfate and the solvent is evaporated off under reduced pressure. 5.7 g of the resulting oil are mixed with 5.7 g of potassium hydroxide, 35 ml of water and 35 ml of absolute ethanol and the mixture is refluxed for 2 hours. The ethanol is evaporated off under reduced pressure, the residue is washed with ethyl acetate, the aqueous phase is acidified with hydrochloric acid and extracted with ethyl acetate, the organic phase is dried over sodium sulfate and the solvent is evaporated off to give the title compound in the form of a semisolid oil.

6b/1-[2-(4-Isobutylphenyl)-2-methylpropionyl]-4-hydroxy-4-(3-trifluoromethylphenyl)piperidine 2.86 g (0.013 mol) of the acid of the previous step, 45 ml of methylene chloride, 2.7 ml (0.0195 mol) of triethylamine, 3.18 g (0.013 mol) of 4-hydroxy-4-(3-trifluoromethylphenyl)piperidine and 5.74 g (0.013 mol) of BOP are mixed and the mixture is stirred at room temperature for 1.5 hours. The solvent is evaporated off under reduced pressure, the residue is taken up with ethyl acetate, the mixture is washed with water, with 1 N hydrochloric acid, with water, with 1 N sodium hydroxide and with water, the organic phase is dried over sodium sulfate and filtered and the solvent is evaporated off to give an oil. This is crystallized from isopropyl ether to give 1.5 g of the title compound. M.p.=158–160° C. Thin layer chromatography (eluent: cyclohexane/ethyl acetate=7/3): Rf=0.4.

6c/1-[2-(4-Isobutylphenyl)-2-methylpropyl]-4-hydroxy-4-(3-trifluoromethylphenyl)piperidine hydrochloride 2.78 g (0.00622 mol) of the compound of the previous step in 30 ml of tetrahydrofuran are heated to the reflux point and 1.9 ml (0.0186 mol) of borane/dimethyl sulfide in 20 ml of tetrahydrofuran are added, reflux being maintained for 4 hours. The solution is cooled to 10–15° C., 15 ml of methanol are added and the mixture is stirred for 15 minutes at room temperature and 30 minutes under reflux. The solvent is evaporated off under reduced pressure, the residue is taken up with water (15 ml), concentrated ammonium hydroxide is added until the pH is basic, the mixture is extracted with ethyl acetate, the extract is washed with water, the organic phase is dried over sodium sulfate and the solvent is evaporated off under reduced pressure to give 3 g of an oil. This is salified by treatment with a saturated solution of hydrochloric acid in isopropanol to give 1.4 g of the title compound. M.p.=263–265° C. Thin layer chromatography (eluent: cyclohexane/ethyl acetate=7/3): Rf=0.3 (base).

6d/1-[2-(4-Isobutylphenyl)-2-methylpropyl]-4-(3-tri-fluoromethylphenyl)-1,2,3,6-tetrahydropyridine oxalate 1.2 g (0.0025 mol) of the compound of the previous step, 10 ml of glacial acetic acid and 3 ml of 96% sulfuric acid are refluxed for 2 hours. The mixture is poured into a water/ice mixture, 20% sodium hydroxide solution is added until the pH is basic, the resulting mixture is extracted with ethyl acetate, the organic phase is washed with water and dried over sodium sulfate and the solvent is evaporated off under reduced pressure to give an oil. This is treated with oxalic acid in isopropanol to give the title compound. M.p.= 164–165° C.

EXAMPLE 7

1-[2-(4-Isopropylphenyl)ethyl]-4-(3-trifluoromethyl-phenyl)-1,2,3,6-tetrahydropyridine hydrochloride 7a/1-Bromo-2-(4-isopropylphenyl)ethane A mixture of 4.6 g (0.030 mol) of cumene, 50 ml of methylene chloride and 2.86 ml (0.033 mol) of bromoacetyl bromide is cooled to 0–5° C. and 4 g (0.030 mol) of aluminum trichloride are added. The mixture is stirred at 0–5° C. for one hour and then stirred at room temperature for 4 hours. It is poured into a water/ice mixture and extracted with methylene chloride, the organic phase is dried over sodium sulfate and the solvent is evaporated off under reduced pressure. 8.5 g of the resulting oil are mixed with 19 ml (0.246 mol) of trifluoroacetic acid and 24.6 ml (0.154 mol) of triethylsilane and the mixture is heated at 80° C. for 4 hours. Saturated aqueous sodium bicarbonate solution is then added until the pH is basic, the mixture is extracted with ethyl acetate, the organic phase is dried over sodium sulfate and the solvent is evaporated off under reduced pressure to give 10 g of the title compound.

7b/1-[2-(4-Isopropylphenyl)ethyl]-4-(3-trifluoro-methylphenyl)-1,2,3,6-tetrahydropyridine hydrochloride A mixture of 3.7 g (0.014 mol) of 4-(3-trifluoro-methylphenyl)-1,2,3,6-tetrahydropyridine, 74 ml of butanol, 4.8 g (0.035 mol) of anhydrous potassium carbonate chips and 4 g (0.018 mol) of the product of the previous step is refluxed for 5 hours. The solvent is evaporated off under reduced pressure, the residue is taken up with ethyl acetate, the mixture is washed with water and dried over sodium sulfate and the solvent is evaporated off under reduced pressure. The hydrochloride of the resulting oil is prepared by treatment with a saturated solution of hydrochloric acid in isopropanol to give 2 g of the title compound, which is crystallized from isopropanol. M.p.=262–263° C. Thin layer chromatography (eluent: cyclohexane/ethyl acetate=1/1): Rf=0.7.

EXAMPLE 8

1-[2-(3'-Chlorobiphenyl-4-yl)ethyl]-4-(3-trifluoro-methylphenyl)-1,2,3,6-tetrahydropyridine 8a/1-Bromo-2-(3'-chlorobiphenyl-4-yl)ethane A mixture of 5 g (0.026 mol) of 3-chlorobiphenyl, 50 ml of methylene chloride and 6.95 g (0.034 mol) of bromoacetyl bromide is cooled to 0–5° C. and 4 g (0.030 mol) of aluminum trichloride are added. The mixture is stirred for 4 hours at room temperature. It is poured into a water/ice mixture and extracted with methylene chloride and the organic phase is washed with 1 N HCl solution, dried over sodium sulfate and evaporated under reduced pressure. 7 g of the resulting oil are mixed with 12.1 ml (0.156 mol) of trifluoroacetic acid and 15.8 ml (0.0986 mol) of triethylsilane and the mixture is heated at 80° C. for 4 hours. Saturated aqueous sodium bicarbonate solution is then added until the pH is basic, the mixture is extracted with ethyl ether, the organic phase is washed with sodium bicarbonate solution and dried over sodium sulfate and the solvent is evaporated off under reduced pressure to give the title compound.

8b/1-[2-(3'-Chlorobiphenyl-4-yl)ethyl]-4-(3-trifluoro-methylphenyl)-1,2,3,6-tetrahydropyridine A mixture of 2.63 g (0.010 mol) of 4-(3-trifluoromethylphenyl)-1,2,3,6-tetrahydropyridine, 80 ml of butanol, 3.5 g (0.025 mol) of anhydrous potassium carbonate chips and 2.63 g of the product of the previous step is refluxed for 5 hours. The salts are filtered off, the solvent is evaporated off under reduced pressure, the residue is taken up with ethyl acetate, the mixture is washed with water and dried over sodium sulfate and the solvent is evaporated off under reduced pressure. The crude product is purified by chromatography on a silica gel column using a 3/7 ethyl acetate/cyclohexane mixture as the eluent. Rf=0.5. 2 g of the title compound are obtained. M.p.=85–87° C.

EXAMPLE 9

1-[2-(2'-Chlorobiphenyl-4-yl)ethyl]-4-(3-trifluoro-methylphenyl)-1,2,3,6-tetrahydropyridine hydrochloride 9a/1-Bromo-2-(2'-chlorobiphenyl-4-yl)ethane 8 g of the title compound are obtained by following the procedure described in Example 8a but using 5 g of 2-chlorobiphenyl instead of 3-chlorobiphenyl.

9b/1-[2-(2'-Chlorobiphenyl-4-yl)ethyl]-4-(3-trifluoro-methylphenyl)-1,2,3,6-tetrahydropyridine hydrochloride Crude 1-[2-(2'-chlorobiphenyl-4-yl)ethyl]-4-(3-tri-fluoromethylphenyl)-1,2,3,6-tetrahydropyridine is obtained by following the procedure described in Example 8b but using the compound of step 9a. This is purified by chromatography on a silica gel column using a 2/8 ethyl acetate/cyclohexane mixture as the eluent; Rf=0.5. The hydrochloride is prepared with a saturated solution of hydrochloric acid in isopropanol. The resulting product is crystallized from isopropanol to give 5 g of the title compound. M.p.=227–230° C.

EXAMPLE 10

1-[2-(4'-Chlorobiphenyl-4-yl)ethyl]-4-(3-trifluoro-methylphenyl)-1,2,3,6-tetrahydropyridine 10a/1-Bromo-2-(4'-chlorobiphenyl-4-yl)ethane The title compound is obtained by following the procedure described in Example 8a but using 5 g of 4-chlorobiphenyl instead of 3-chlorobiphenyl.

10b/1-[2-(4'-Chlorobiphenyl-4-yl)ethyl]-4-(3-tri-fluoromethylphenyl)-1,2,3,6-tetrahydropyridine The crude title compound is obtained by following the procedure described in Example 8b but using the compound of step 10a. This is purified by chromatography on a silica gel column using a 2/8 ethyl acetate/cyclohexane mixture as the eluent; Rf=0.5. 4 g of the title compound are obtained in the form of a white solid, which is crystallized from ethyl acetate. M.p.=146–148° C.

EXAMPLE 11

1-[2-(4'-Fluorobiphenyl-4-yl)ethyl]-4-(3-trifluoro-methylphenyl)-1,2,3,6-tetrahydropyridine hydrochloride 11a/1-Bromo-2-(4'-fluorobiphenyl-4-yl)ethane The title compound is obtained by following the procedure described in Example 8a but using 4-fluorobiphenyl instead of 3-chlorobiphenyl.

11b/1-[2-(4'-Fluorobiphenyl-4-yl)ethyl]-4-(3-tri-fluoromethylphenyl)-1,2,3,6-tetrahydropyridine hydrochloride Crude 1-[2-(4'-fluorobiphenyl-4-yl)ethyl]-4-(3-trifluoromethylphenyl)-1,2,3,6-tetrahydropyridine is obtained by following the procedure described in Example 8b but using the compound of step 11a. The hydrochloride is prepared with a saturated solution of HCl in isopropanol. This gives the title compound, which is crystallized from isopropanol. M.p.=257–259° C. Thin layer chromatography (eluent: cyclohexane/ethyl acetate=1/1): Rf=0.5.

EXAMPLE 12

1-[2-(3'-Trifluoromethylbiphenyl-4-yl)ethyl]-4-(3-tri-fluoromethylphenyl)-1,2,3,6-tetrahydropyridine hydrochloride The title compound is obtained by following the procedure described in Example 8 but starting from 3-trifluoromethylbiphenyl instead of 3-chlorobiphenyl. M.p.=229–233° C.

EXAMPLE 13

1-[2-(4-Cyclohexylphenyl)ethyl]-4-(3-trifluoromethyl-phenyl)-1,2,3,6-tetrahydropyridine hydrochloride 13a/1-Bromo-2-(4-cyclohexylphenyl)ethane 5.56 g of the title compound are obtained by following the procedure described in Example 8a but using 10 g of cyclohexylbenzene instead of 3-chlorobiphenyl.

13b/1-[2-(4-Cyclohexylphenyl)ethyl]-4-(3-trifluoro-methylphenyl)-1,2,3,6-tetrahydropyridine hydrochloride Crude 1-[2-(4-cyclohexylphenyl)ethyl]-4-(3-tri-fluoromethylphenyl)-1,2,3,6-tetrahydropyridine is obtained by following the procedure described in Example 8b but using the compound of step 13a. This is purified by chromatography on a silica gel column using a 9/1 cyclohexane/ethyl acetate mixture as the eluent. The hydrochloride is prepared with a saturated solution of hydrochloric acid in isopropanol to give 2.55 g of the title compound. M.p.=255–260° C. Thin layer chromatography (eluent: cyclohexane/ethyl acetate=7/3): Rf=0.5.

EXAMPLE 14

1-[2-(Biphenyl-4-yl)-2-ethyl]-4-(4-fluorophenyl)-1,2,3,6-tetrahydropyridine oxalate A mixture of 1 g (0.0047 mol) of 4-(4-fluorophenyl)-1,2,3,6-tetrahydropyridine, 20 ml of butanol, 1.6 g (0.012 mol) of anhydrous potassium carbonate chips and 1.2 g of 1-bromo-2-(biphenyl-4-yl)ethane is refluxed for 5 hours. The salts are filtered off, the solvent is evaporated off under reduced pressure, the residue is taken up with ethyl acetate, the mixture is washed with water and dried over sodium sulfate and the solvent is evaporated off under reduced pressure. The oxalate of the resulting oil is prepared by treatment with oxalic acid in acetone. This gives the title compound, which is crystallized from ethanol. M.p.=211–215° C. Thin layer chromatography (eluent: ethyl acetate/cyclohexane=1/1): Rf=0.6.

EXAMPLE 15

1-[2-(Biphenyl-4-yl)-2-methylpropyl]-4-(3-trifluoro-methylphenyl)-1,2,3,6-tetrahydropyridine hydrochloride 15a/Ethyl biphenyl-4-ylacetate 45 g of biphenyl-4-ylacetic acid (0.212 mol) are dissolved in 650 ml of absolute ethanol. Gaseous hydrochloric acid is bubbled into the solution for 1 hour and the solution is then refluxed for 2 hours. The ethanol is evaporated off, the residue is taken up with ethyl acetate and the mixture is washed with aqueous sodium bicarbonate solution and then with water. The organic phase is dried over sodium sulfate and the solvent is evaporated off under reduced pressure to give 40 g of the title compound.

15b/α,α-Dimethylbiphenyl-4-ylacetic acid 10.8 g (0.0449 mol) of the product of the previous step are dissolved in 100 ml of dimethylformamide. The mixture is cooled to 0–5° C. and 5.04 g of 55% sodium hydride are added in small portions. The mixture is stirred at room temperature for 30 minutes. It is cooled again to 0–5° C., 7.9 ml of methyl iodide are added dropwise and the mixture is stirred at room temperature for 3 hours. It is poured into a water/ice mixture and extracted with ethyl acetate, the extract is washed with water, the organic phase is dried over sodium sulfate and the solvent is evaporated off under reduced pressure. The resulting oil is dissolved in a solution of 12 g of sodium hydroxide in 70 ml of water and 70 ml of 95% ethanol. The reaction medium is refluxed for 2 hours, the ethanol is evaporated off under reduced pressure and the aqueous phase is washed with ethyl acetate. The aqueous solution is acidified with concentrated hydrochloric acid and the precipitate formed is filtered off to give 8.2 g of the title compound, which is crystallized from 500 ml of 50% ethanol. M.p.=152–157° C.

15c/1-[2-(Biphenyl-4-yl)-2-methylpropionyl]-4-hydroxy-4-(3-trifluoromethylphenyl)pyridine 3.6 g (0.015 mol) of the product of the previous step, 60 ml of methylene chloride, 6.3 ml (0.045 mol) of triethylamine, 4.2 g (0.015 mol) of 4-(3-trifluoromethylphenyl)-4-piperidinol hydrochloride and 6.6 g (0.015 mol) of BOP are mixed and the mixture is stirred at room temperature for 1.5 hours. The solvent is evaporated off under reduced pressure, the residue is taken up with ethyl acetate and the mixture is washed with water, then with 1 N hydrochloric acid solution, with water, with 1 N sodium hydroxide solution and again with water. The organic phase is dried over sodium sulfate and the solvent is evaporated off under reduced pressure to give an oil, which is taken up with ethyl acetate. Silica gel is added to the solution and the mixture is stirred for 15 minutes. It is filtered and the solvent is evaporated off under reduced pressure to give 6.3 g of the title compound.

15d/1-[2-(Biphenyl-4-yl)-2-methylpropyl]-4-hydroxy-4-(3-trifluoromethylphenyl)piperidine The product of the previous step is dissolved in 70 ml of anhydrous tetrahydrofuran. The solution is heated to the reflux point and a solution of 3.7 ml (0.039 mol) of borane/dimethylsulfide in 45 ml of anhydrous tetrahydrofuran is added dropwise. The mixture is refluxed for 4 hours and then cooled to 10–15° C. and 15 ml of methanol are added cautiously. The mixture is stirred for 15 min at room temperature and then for 30 min under reflux. The solvent is evaporated off under reduced pressure, the residue is taken up with 15 ml of water, ammonium hydroxide is added until the pH is basic, and the mixture is extracted with ethyl acetate. The organic phase is washed with water and dried over sodium sulfate and the solvent is evaporated off under reduced pressure to give the title compound, which is crystallized from 50 ml of methanol. M.p.=270–272° C.

15e/1-[2-(Biphenyl-4-yl)-2-methylpropyl]-4-(3-tri-fluoromethylphenyl)-1,2,3,6-tetrahydropyridine hydrochloride 1.7 g (0.0035 mol) of the product of the previous step, 14.6 ml of glacial acetic acid and 4.4 ml of 96% sulfuric acid are mixed. The mixture is refluxed for two hours and then poured into a water/ice mixture. Sodium hydroxide is added until the pH is basic, the mixture is extracted with ethyl acetate, the extract is dried over sodium sulfate and the solvent is evaporated off under reduced pressure. The hydrochloride is prepared with a saturated solution of hydrochloric acid in isopropanol. M.p.=238–240° C.

EXAMPLE 16

1-[2-(4-Phenoxyphenyl)-2-ethyl]-4-(3-trifluoromethyl-phenyl)-1,2,3,6-tetrahydropyridine hydrochloride 16a/1-Bromo-2-(4-phenoxyphenyl)ethane A mixture of 3.31 g (0.038 mol) of bromoacetyl bromide, 50 ml of methylene chloride and 5 g (0.029 mol) of diphenyl ether is cooled to 0–5° C. and 4.42 ml (0.033 mol) of aluminum chloride are added. The mixture is stirred at room temperature for 4 hours. It is poured into a-water/ice mixture, the two phases are separated and the organic phase is washed with 1 N hydrochloric acid and with water. The organic phase is dried over sodium sulfate and the solvent is evaporated off under reduced pressure. The residue is purified by chromatography on a silica gel column using a 7/3 cyclohexane/ethyl acetate mixture as the eluent. The fraction of the medium corresponding to 3.2 g of 2-(4-phenoxyphenyl)acetyl bromide is isolated. The resulting oil is mixed with 5.9 ml (0.077 mol) of trifluoroacetic acid and 7.7 ml (0.048 mol) of triethylsilane. The mixture is heated at 80° C. for 4 hours and the residue is taken up with an ethyl ether/sodium bicarbonate mixture. The two phases are separated, the organic phase is dried over sodium sulfate and the solvent is evaporated off under reduced pressure to give 7 g of the title compound.

16b/1-[2-(4-Phenoxyphenyl)-2-ethyl]-4-(3-trifluoro-methylphenyl)-1,2,3,6-tetrahydropyridine hydrochloride A mixture of 2.63 g (0.010 mol) of 4-(3-trifluoro methylphenyl)-1,2,3,6-tetrahydropyridine, 80 ml of butanol, 3.5 g (0.025 mol) of anhydrous potassium carbonate chips and 3.05 g (0.011 mol) of the product of the previous step is refluxed for 5 hours. The salts are filtered off, the solvent is evaporated off under reduced pressure, the residue is taken up with ethyl acetate, the mixture is washed with water and dried over sodium sulfate and the solvent is evaporated off under reduced pressure. The crude product is purified by chromatography on a silica gel column using a 3/7 ethyl acetate/cyclohexane mixture as the eluent. The product of Rf≈0.5 is isolated. The hydrochloride is prepared with a saturated solution of hydrochloric acid in isopropanol. M.p.=196–198° C.

EXAMPLE 17

1-[2-(4-Benzylphenyl)-2-ethyl]-4-(3-trifluoromethyl-phenyl)-1,2,3,6-tetrahydropyridine hydrochloride 17a/1-Bromo-2-(4-benzylphenyl)ethane A mixture of 2.7 g (0.030 mol) of bromoacetyl bromide, 54 ml of methylene chloride and 4 g (0.0238 mol) of diphenylmethane is cooled to 0–5° C. and 3.7 ml (0.0274 mol) of aluminum chloride are added. The mixture is stirred at room temperature for 4 hours. It is poured into a water/ice mixture and the two phases are separated. The organic phase is dried over sodium sulfate and the solvent is evaporated off under reduced pressure. The residue is taken up with iso-propyl ether, the mixture is stirred and the precipitate formed is filtered off. 4.5 g of 2-(4-benzylphenyl)acetyl bromide are isolated. The resulting product is mixed with 8 ml of trifluoroacetic acid and 4.57 ml (0.048 mol) of triethylsilane. The mixture is heated at 80° C. for 4 hours and the residue is taken up with an ethyl ether/sodium bicarbonate mixture. The two phases are separated, the organic phase is dried over sodium sulfate and the solvent is evaporated off under reduced pressure to give 6.5 g of the title compound, which is purified by chromatography on a silica gel column using a 9/1 cyclohexane/ethyl acetate mixture as the eluent. The first eluted fraction, which corresponds to the title compound, is isolated.

17b/1-[2-(4-Benzylphenyl)-2-ethyl]-4-(3-trifluoro-methylphenyl)-1,2,3,6-tetrahydropyridine hydrochloride A mixture of 2.6 g (0.0098 mol) of 4-(3-trifluoro-methylphenyl)-1,2,3,6-tetrahydropyridine, 80 ml of butanol, 3.4 g (0.0246 mol) of anhydrous potassium carbonate chips and 3 g of the product of the previous step is refluxed for 5 hours. The salts are filtered off, the solvent is evaporated off under reduced pressure, the residue is taken up with ethyl acetate, the mixture is washed with water and dried over sodium sulfate and the solvent is evaporated off under reduced pressure. The crude product is purified by chromatography on a silica gel column using a 3/7 ethyl acetate/cyclohexane mixture as the eluent. 2 g of base are isolated. The hydrochloride is prepared with a saturated solution of hydrochloric acid in isopropanol to give the title compound, which is crystallized from acetone. M.p.=169–172° C.

EXAMPLE 18

1-[2-(4-n-Butylphenyl)ethyl]-4-(3-trifluoromethyl -phenyl)-1,2,3,6-tetrahydropyridine oxalate 18a/1-Bromo-2-(4-n-butylphenyl)ethane 2.5 g of the title compound are obtained by following the procedure described in Example 8a but using 4.7 ml (0.030 mol) of n-butylbenzene instead of 3-chlorobiphenyl. Thin layer chromatography (eluent: cyclohexane): Rf=0.4.

18b/1-[2-(4-n-Butylphenyl)ethyl]-4-(3-trifluoromethyl -phenyl)-1,2,3,6-tetrahydropyridine oxalate Crude 1-[2-(4-n-butylphenyl)ethyl]-4-(3-trifluoro-methylphenyl)-1,2,3,6-tetrahydropyridine is obtained by following the procedure described in Example 8b but using the compound of step 18a. This is purified by chromatography on a silica gel column using a 1/1 ethyl acetate/cyclohexane mixture as the eluent. The oxalate is prepared with oxalic acid in acetone. The resulting product is crystallized from isopropanol to give 1.18 g of the title compound. M.p.=162–165° C.

EXAMPLE 19

1-[2-(Biphenyl-4-yl)ethyl]-4-(3-trifluoromethylphenyl)-1,2,3,6-tetrahydropyridine and its hydrochloride 19a/Ethyl biphenyl-4-ylacetate The title compound is obtained by following the procedure described in Example 1a using biphenyl-4-ylacetic acid instead of 2-(4-isobutylphenyl)propionic acid.

19b/Biphenyl-4-ylethyl alcohol

The title compound is obtained by following the procedure described in Example 1b using the product of step 19a. M.p.=75–30° C.

19c/2-(Biphenyl-4-yl)ethyl methanesulfonate

The title compound is obtained by following the procedure described in Example 1c using the product of step 19b. M.p.=75–77° C.

19d/1-[2-(Biphenyl-4-yl)ethyl]-4-(3-trifluoromethyl -phenyl)-1,2,3,6-tetrahydropyridine and its hydrochloride A mixture of 8.3 g (0.03 mol) of the product of the previous step, 100 ml of isopropanol, 12.8 ml (0.0915 mol) of triethylamine and 7.91 g (0.03 mol) of 4-(3-trifluoromethylphenyl)-1,2,3,6-tetrahydropyridine is refluxed for 8 hours. The solvent is evaporated off under reduced pressure and the residue is taken up with 70 ml of ethyl acetate. The mixture is washed twice with water and dried over sodium sulfate and the solvent is evaporated off under reduced pressure to give 1-[2-(biphenyl-4-yl)ethyl]-4-(3-trifluoromethylphenyl)-1,2,3,6-tetrahydropyridine, which is crystallized from 30 ml of isopropanol. M.p.=114–116° C.

The hydrochloride is prepared with a saturated solution of hydrochloric acid in isopropanol to give the title compound, which is crystallized from 95% ethanol. M.p.=262–263° C.

EXAMPLE 20

1-[2-(4-n-Butoxyphenyl)ethyl]-4-(3-trifluoromethyl -phenyl)-1,2,3,6-tetrahydropyridine hydrochloride 20a/1-[2-(4-Hydroxyphenyl)ethyl]-4-(3-trifluoromethyl -phenyl)-1,2,3,6-tetrahydropyridine and its hydrochloride A mixture of 5.6 g (0.0211 mol) of 4-(3-trifluoro-methylphenyl)-1,2,3,6-tetrahydropyridine, 7.3 g (0.0528 mol) of potassium carbonate, 112 ml of amyl alcohol and 3.3 g (0.0211 mol) of 4-hydroxyphenethyl chloride is refluxed for 5 hours. Any salts are filtered off, the solvent is evaporated off under reduced pressure, the residue is taken up with ethyl acetate, the mixture is washed with water, the organic phase is dried over sodium sulfate and the solvent is evaporated off under reduced pressure. The hydrochloride is prepared with a saturated solution of hydrochloric acid in isopropanol to give 3 g of the title compound. M.p.=220–222° C.

20b/1-[2-(4-n-Butoxyphenyl)ethyl]-4-(3-trifluoro-methylphenyl)-1,2,3,6-tetrahydropyridine hydrochloride A mixture of 1 g (0.0029 mol) of the compound of the previous step in the form of the base, 15 ml of DMSO and 150 mg (0.0038 mol) of 60% sodium hydride is stirred for 2 hours at room temperature. 0.4 ml (0.0038 mol) of 1-bromobutane and 150 mg (0.001 mol) of potassium iodide are added to the reaction mixture, which is stirred for a further two hours at room temperature. It is poured into a water/ice mixture and extracted with ethyl acetate, the organic phase is dried over sodium sulfate and the solvent is evaporated off under reduced pressure. The hydrochloride is prepared with a saturated solution of hydrochloric acid in isopropanol to give 500 mg of the title compound. M.p.=212–214° C.

EXAMPLE 21

1-[2-(4-(3-Ethoxycarbonylpropoxy)phenyl)ethyl]-4-(3-trifluoromethylphenyl)-1,2,3,6-tetrahydropyridine hydrochloride The procedure described in Example 20b is followed using ethyl 4-bromobutyrate instead of 1-bromobutane. This gives the title compound, which is crystallized from isopropanol. M.p.=204–205° C.

| Elemental analysis | % C   | % H  | % N  |
| --- | --- | --- | --- |
| calculated | 62.71 | 6.27 | 2.81 |
| found      | 62.69 | 6.34 | 2.80 |

EXAMPLE 22

1-[2-(Biphenyl-4-yl)ethyl]-4-(6-chloropyrid-2-yl)-1,2,3,6-tetrahydropyridine 22a/(1-Benzyl-1,2,3,6-tetrahydropyrid-4-yl)tributyl-stannane A mixture of 15.85 g (0.0837 mol) of 1-benzyl-4-piperidone in 140 ml of anhydrous dimethoxyethane and 25 g (0.0837 mol) of trisilidrazine in 140 ml of anhydrous dimethoxyethane is stirred at room temperature for 3 hours.

The solvent is evaporated off under reduced pressure. The residue is taken up with 420 ml of anhydrous hexane, and 420 ml of anhydrous tetramethylethylenediamine are added. The mixture is cooled to −78° C. and 156 ml of n-butyllithium (0.25 mol) (1.6 M solution in hexane) are added dropwise. After about 30 minutes the temperature is allowed to rise to 0° C. and the mixture is stirred for 15 minutes. 45 ml (0.167 mol) of tributylstannane chloride are then added to the reaction mixture. After 1 hour a water/ice mixture is added extremely cautiously. The reaction medium is extracted with ethyl ether, the organic phase is washed with water and dried over sodium sulfate and the solvent is evaporated off under reduced pressure. This gives 70 g of crude product, which is purified by chromatography on a silica gel column using a 95/5 cyclohexane/ethyl acetate mixture as the eluent to give the title compound in the form of an oil.

$^1$H NMR (CDCl$_3$)-δ(ppm): 0.84 (9H; m: CH$_3$); 1.19–1.58 (18H; m: CH$_2$ -chain); 2.31 (2H; m); 2.53 (2H; m); 3.02 (2H; m); 3.56 (2H; s: benzyl methylene); 5.76 (1H; m*); 7.14–7.18 (5H; m: arom.).

satellite bands: $^3J_{cis}$($^1$H-$^{117}$Sn) and $^3J_{cis}$($^1$H-$^{119}$Sn).

22b/1-Benzyl-4-(6-chloropyrid-2-yl)-1,2,3,6-tetrahydropyridine 18.5 g (0.04 mol) of the compound of the previous step are dissolved in 200 ml of anhydrous dimethylformamide under a nitrogen atmosphere. 11.8 g (0.08 mol) of 2,6-dichloropyridine, 0.64 g of Pd(II)(Ph$_3$P)$_2$Cl$_2$, 4.38 g (0.04 mol) of tetramethylammonium chloride and 2.76 g (0.02 mol) of potassium carbonate are added to the solution. The mixture is heated at 110° C. for 6 hours and then poured into 100 ml of 5% sulfuric acid solution. It is extracted with ethyl ether, ammonium hydroxide is added to the aqueous phase until the pH is basic, and the mixture is extracted with ethyl acetate. The combined organic phases are dried over sodium sulfate and the solvent is evaporated off under reduced pressure. The residue is purified by chromatography on a silica gel column using a 1/1 cyclohexane/ethyl acetate mixture as the eluent to give the title compound. M.p.=100–102° C.

22c/4-(6-Chloropyrid-2-yl)-1,2,3,6-tetrahydropyridine hydrochloride

A solution of 7.0 g (0.024 mol) of the compound of the previous step in 110 ml of dichloroethane is cooled to 0–5° C. and 5.8 ml (0.054 mol) of chloroethylchloroformate are added. The mixture is stirred for 5 minutes and then refluxed for 1.5 hours. The solvent is evaporated off under reduced pressure, the residue is taken up with 100 ml of methanol and the mixture is refluxed for 1 hour. The solvent is evaporated off, the residue is taken up with isopropanol and the solid is filtered off to give the title compound, which is crystallized from 90% ethanol. M.p.=305–307° C.

22d/1-[2-(Biphenyl-4-yl)ethyl]-4-(6-chloropyrid-2-yl)-1,2,3,6-tetrahydropyridine A mixture of 1.35, g (0.0053 mol) of 4-(2-bromo-ethyl) biphenyl, 25 ml of butanol, 1.72 g (0.0125 mol) of anhydrous potassium carbonate chips and 1.16 g (0.005 mol) of the product of the previous step is refluxed for 6 hours. The solvent is evaporated off under reduced pressure, the residue is taken up with ethyl acetate, the mixture is washed with water and dried over sodium sulfate and the solvent is evaporated off under reduced pressure. The residue is taken up with 30 ml of isopropyl ether and the precipitate formed is filtered off to give the title compound, which is recrystallized from isopropanol. M.p.=135–136° C.

EXAMPLE 23

1-[2-(2,3'-Dichlorobiphenyl-4-yl)ethyl]-4-(3-trifluoro-methylphenyl)-1,2,3,6-tetrahydropyridine hydrochloride 23a/Ethyl (3-chloro-4-trifluoromethylsulfonylphenyl) acetate Gaseous hydrochloric acid is bubbled into a solution of 5 g (27 mmol) of (3-chloro-4-hydroxyphenyl)acetic acid in 60 ml of ethanol, with cooling in an ice bath for one hour, and the mixture is then refluxed for 5 hours. The solvent is evaporated off, the residue is taken up with saturated aqueous sodium bicarbonate solution and the mixture is extracted with ethyl acetate. The extract is filtered, the organic phase is dried over sodium sulfate and the solvent is evaporated off under reduced pressure. The crude product is purified by chromatography on a silica gel column using a 7/3 cyclohexane/ethyl acetate mixture as the eluent to give ethyl 3-chloro-4-hydroxyphenyl acetate.

4 g (18.6 mmol) of this compound are dissolved in 14 ml of pyridine, and 3.36 ml (20 mmol) of triflic anhydride are added dropwise under a nitrogen atmosphere, the temperature being maintained at 0° C. for 1 hour. The mixture is poured into ice and extracted with ethyl acetate. The organic phase is dried over sodium sulfate and filtered and the solvent is evaporated off under reduced pressure. The crude product is purified by chromatography on a silica gel column using a 9/1 cyclohexane/ethyl acetate mixture as the eluent to give the title compound.

23b/Ethyl (2,3'-dichlorobiphenyl-4-yl)acetate

A mixture of 4.9 g (14 mmol) of the product of the previous step, 2.45 g (16 mmol) of 3-chlorobenzeneboronic acid, 63 mg (0.28 mmol) of palladium acetate, 4.84 g (35 mmol) of potassium carbonate and 4.5 g (14 mmol) of tetrabutylammonium bromide in 19 ml of water is stirred at 70° C. for 1 hour. It is allowed to cool and extracted with ethyl acetate. The organic phase is dried over sodium sulfate and filtered and the solvent is evaporated off under reduced pressure. The crude reaction product is purified by chromatography on a silica gel column using a 9/1 cyclohexane/ethyl acetate mixture as the eluent to give the title compound in the form of an oil.

23c/(2,3'-Dichlorobiphenyl-4-yl) acetic acid

A mixture of the product obtained in the previous step and 1.57 g (28 mmol) of potassium hydroxide in 39 ml of methanol is heated at 80° C. for 2 hours. The solvent is evaporated off under reduced pressure and the residue is washed with 1 N hydrochloric acid solution and extracted with methylene chloride. The organic phase is dried over sodium sulfate and filtered and the solvent is evaporated off under reduced pressure. The crude product is treated with hexane to give a white precipitate. This is filtered off and crystallized from a hexane/ethyl acetate mixture to give 1.4 g of the title product. M.p.=92–94° C.

23d/1-[(2,3'-Dichlorobiphenyl-4-yl)acetyl]-4-hydroxy-4-(3-trifluoromethylphenyl)piperidine A mixture of 1.2 g (4.3 mmol) of the product of the previous step, 1.2 g (4.3 mmol) of 4-hydroxy-4-(3-trifluoromethylphenyl)piperidine, 17.2 ml of methylene chloride, 1.54 ml (11 mmol) of triethylamine and 1.9 g (4.3 mmol) of BOP is stirred at room temperature for 24 hours. It is poured into water and extracted with methylene chloride and the organic phase is washed with 1 N hydrochloric acid solution, with water, with 1 N sodium hydroxide solution and again with water. The organic phase is dried over sodium sulfate and filtered and the solvent is evaporated off under reduced pressure. The crude product is purified by chromatography on a silica gel column using a 1/1 cyclohexane/ethyl acetate mixture as the eluent to give the title product in the form of a white solid. M.p.=154–155° C.

23e/1-[2-(2,3'-Dichlorobiphenyl-4-yl)ethyl]-4-hydroxy-4-(3-trifluoromethylphenyl)piperidine 1.6 g (3.15 mmol) of the compound of the previous step in 17 ml of tetrahydrofuran are heated to the reflux point and 0.92 ml (9.3 mmol) of borane/dimethyl sulfide in 12 ml of tetrahydrofuran is added, reflux being maintained for 4 hours. The solution is cooled to 0° C., 15 ml of methanol are added and the mixture is stirred for 30 minutes under reflux. The solvent is evaporated off under reduced pressure, the residue is taken up with water (15 ml), concentrated ammonium hydroxide is added until the pH is basic, the mixture is extracted with ethyl acetate, the organic phase is washed with water and dried over sodium sulfate and the solvent is evaporated off under reduced pressure. The product is purified by chromatography on a silica gel column using a 1/1 cyclohexane/ethyl acetate mixture as the eluent to give 1.2 g of the title product in the form of an oil.
23f/1-[2-(2,3'-Dichlorobiphenyl-4-yl)ethyl]-4-(3-tri-fluoromethylphenyl)-1,2,3,6-tetrahydropyridine hydrochloride 1.2 g (2.43 mmol) of the compound of the previous step, 12.7 ml of glacial acetic acid and 3 ml of 96% sulfuric acid are heated at 100° C. for 1 hour. The mixture is poured into a water/ice mixture, 20% sodium hydroxide solution is added until the pH is basic, the resulting mixture is extracted with ethyl acetate, the organic phase is washed with water and dried over sodium sulfate and the solvent is evaporated off under reduced pressure. The product is purified by chromatography on a silica gel column using a 7/3 cyclohexane/ethyl acetate mixture as the eluent. The hydrochloride of the resulting product is prepared with a saturated solution of hydrochloric acid in isopropanol.

A white solid is obtained. M.p.=204–206° C.

EXAMPLE 24

1-[2-(3-Chlorobiphenyl-4-yl)ethyl]-4-(3-trifluoro-methylphenyl)-1,2,3,6-tetrahydropyridine hydrochloride
24a/Ethyl (2-chloro-4-trifluoromethylsulfonylphenyl) acetate The title compound is obtained by following the procedure described in Example 23a but using (2-chloro-4-hydroxyphenyl)acetic acid, prepared according to Preparation 4, instead of (3-chloro-4-hydroxyphenyl)acetic acid.
24b/Ethyl (3-chlorobiphenyl-4-yl)acetate The title compound is obtained by following the procedure described in Example 23b but using the product of the previous step instead of the product of step 23a and benzeneboronic acid instead of 3-chlorobenzeneboronic acid.
24c/(3-Chlorobiphenyl-4-yl)acetic acid The title compound is obtained by following the procedure described in Example 23c but using the ester of the previous step.
24d/1-[(3-Chlorobiphenyl-4-yl)acetyl]-4-hydroxy-4-(3-trifluoromethylphenyl)piperidine The title compound is obtained by following the procedure described in Example 23d but using the product of the previous step instead of the product of step 23c.
24e/1-[2-(3-Chlorobiphenyl-4-yl)ethyl]-4-hydroxy-4-(3-trifluoromethylphenyl)piperidine The title compound is obtained by following the procedure described in Example 23e but using the product of the previous step instead of the product of step 23d.
24f/1-[2-(3-Chlorobiphenyl-4-yl)ethyl]-4-(3-trifluoro-methylphenyl)-1,2,3,6-tetrahydropyridine hydrochloride The title compound is obtained by following the procedure described in Example 23f but using the product of the previous step instead of the product of step 23e. M.p.=227° C.

EXAMPLE 25

1-[2-(3',5'-Dichlorobiphenyl-4-yl)ethyl]-4-(3-tri-fluoromethylphenyl)-1,2,3,6-tetrahydropyridine hydrochloride
25a/2-(31,5'-Dichlorobiphenyl-4-yl)ethanol The title compound is obtained by following the procedure described in Example 23b but using 2-(p-bromophenyl) ethanol instead of ethyl (3-chloro-4-trifluoromethyl-sulfonylphenyl)acetate and 3,5-dichlorobenzeneboronic acid instead of 3-chlorobenzeneboronic acid.
25b/2-(3',5'-Dichlorobiphenyl-4-yl)ethyl methanesulfonate The title compound is obtained by following the procedure described in Example 1c but using the product of the previous step instead of 2-(4-isobutylphenyl)propyl alcohol.
25c/1-[2-(3',5'-Dichlorobiphenyl-4-yl)ethyl]-4-(3-tri-fluoromethylphenyl)-1,2,3,6-tetrahydropyridine hydrochloride The title compound is obtained by following the procedure described in Example 1d but using the product of the previous step instead of 2-(4-isobutylphenyl)propyl methanesulfonate. M.p.=200–202° C.

EXAMPLE 26

1-[2-(2',4'-Dichlorobiphenyl-4-yl)ethyl]-4-(3-tri-fluoromethylphenyl)-1,2,3,6-tetrahydropyridine hydrochloride The title compound is obtained by following the procedure described in Example 25 but using 2,4-dichlorobenzeneboronic acid instead of 3,5-dichlorobenzeneboronic acid. M.p.=204–206° C.

EXAMPLE 27

1-[2-(2-Chlorobiphenyl-4-yl)ethyl]-4-(3-trifluoro-methylphenyl)-1,2,3,6-tetrahydropyridine hydrochloride
27a/(2-Chlorobiphenyl-4-yl) acetic acid By following the procedure described in Example 23b but using benzeneboronic acid instead of 3-chlorobenzeneboronic acid, the title compound is obtained in the form of a solid, which is crystallized from ethyl acetate. M.p.=103–105° C.
27b/1-[(2-Chlorobiphenyl-4-yl)acetyl]-4-hydroxy-4-(3-trifluoromethylphenyl)piperidine The title compound is obtained by following the procedure described in Example 23d but using the compound of the previous step instead of (2,3'-dichlorobiphenyl-4-yl) acetic acid. M.p.=46–490C.
27c/1-[2-(2-Chlorobiphenyl-4-yl)ethyl]-4-(3-trifluoro-methylphenyl)-1,2,3,6-tetrahydropyridine hydrochloride The title compound is obtained by following the procedure described in Examples 23e and 23f but using the product of the previous step instead of 1-[(2,3'-dichlorobiphenyl-4-yl)acetyl]-4-hydroxy-4-(3-trifluoromethylphenyl)piperidine. M.p.=210–212° C.

EXAMPLE 28

1-[2-(3'-Chlorobiphenyl-4-yl)-2-methylpropyl]-4-(3-trifluoromethylphenyl)-1,2,3,6-tetrahydropyridine hydrochloride 28a/Ethyl 2-(4-bromophenyl)-2-methylpropionate 7.5 g (31 mmol) of ethyl 4-bromophenylacetate are dissolved in 120 ml of DMF, and 2.5 g of sodium hydride (60% dispersion in oil) are added slowly. The mixture is stirred at room temperature for 30 minutes and then cooled to 100° C., 4.1 ml (61 mmol) of methyl iodide are added and the mixture is stirred at room temperature for 4 hours. It is poured into a water/ice mixture and extracted with ethyl acetate, the organic phase is dried over sodium sulfate and filtered and the solvent is evaporated off under reduced pressure. The crude product is purified by chromatography on a silica gel column using a 95/5 cyclohexane/ethyl acetate mixture as the eluent to give the title compound.
28b/2-(3'-Chlorobiphenyl-4-yl) -2-methylpropionic acid A mixture of 2.18 g (8 mmol) of the product of the previous step, 1.38 g (8.8 mmol) of 3-chlorobenzeneboronic acid, 2.16 g (20 mmol) of potassium bicarbonate, 2.58 g (8 mmol) of tetrabutylammonium bromide and 40 mg of palladium acetate in 11 ml of water is heated at 70° C. for 3 hours under an argon atmosphere. After cooling, it is extracted with ethyl acetate. The organic phase is dried over sodium sulfate and filtered and the solvent is evaporated off under reduced pressure.

The crude reaction product is purified by chromatography on a silica gel column using a 9/1 cyclohexane/ethyl acetate mixture as the eluent to give 1.85 g of the ethyl ester of the title acid. This product is mixed with 0.7 g of potassium hydroxide in 14 ml of methanol and the mixture is heated at 80° C. for 3 hours. The solvent is evaporated off and the residue is poured into water. The mixture is acidified with 1 N hydrochloric acid solution. It is extracted with methylene chloride, the organic phase is dried over sodium sulfate and filtered and the solvent is evaporated off under reduced pressure. The solid obtained is crystallized from a hexane/ethyl acetate mixture to give 1 g of the title compound in the form of a white solid. M.p.=145–146° C.

28c/1-[2-(3'-Chlorobiphenyl-4-yl)-2-methylpropyl]-4-(3-trifluoromethylphenyl)-1,2,3,6-tetrahydropyridine hydrochloride The title compound is obtained by following the procedure described in Examples 23d, 23e and 23f but using the compound of the previous step instead of (2,3'-dichlorobiphenyl-4-yl)acetic acid. M.p.=215–217° C.

EXAMPLE 29

1-[2-(2-Fluorobiphenyl-4-yl)propyl]-4-(3-trifluoro-methylphenyl)-1,2,3,6-tetrahydropyridine hydrochloride The title compound is obtained by following the procedure described in Examples 23d, 23e and 23f but using flurbiprofen instead of (2,3'-dichlorobiphenyl-4-yl)acetic acid. M.p.=181–183° C. (free base); m.p.=204–206° C. (hydrochloride).

EXAMPLE 30

1-[2-(4-Methoxybiphenyl-3-yl)ethyl]-4-(3-trifluoro-methylphenyl)-1,2,3,6-tetrahydropyridine hydrochloride and 1-[2-(4'-methoxybiphenyl-4-yl)ethyl]-4-(3-tri-fluoromethylphenyl)-1,2,3,6-tetrahydropyridine 11.5 g (0.0652 mol) of 4-methoxybiphenyl, 50 ml of dichloroethane and 5.42 g (0.0625 mol) of bromoacetyl bromide are mixed. The mixture is cooled to -10° C. and 9.3 g (0.070 mol) of aluminum trichloride are added. The mixture is stirred at −10° C. for 2 hours and acidified with 1 N hydrochloric acid solution, the two phases are separated and the aqueous phase is extracted with ethyl acetate. The combined organic phases are dried over sodium sulfate, the solvent is evaporated off under reduced pressure and the crude product is purified by chromatography on a silica gel column using a 9/1 cyclohexane/ethyl acetate mixture as the eluent. A fraction of Rf≈0.3, consisting of a 75:25 mixture of the 3-bromoacetyl-4-methoxybiphenyl and 4'-bromoacetyl-4-methoxybiphenyl isomers, is isolated. 5.8 g (0.019 mol) of the above isomer mixture in 11.6 ml of trifluoroacetic acid and 5.8 ml of triethylsilane are refluxed for 3 hours. The mixture is poured into ice, 1 N sodium hydroxide solution is added until the pH is basic, and the mixture is extracted with ethyl acetate. The organic phase is dried over sodium sulfate and the solvent is evaporated off under reduced pressure. The residue is taken up with 160 ml of butanol, and 5.1 g (0.019 mol) of 4-(3-trifluoromethylphenyl)-1,2,3,6-tetrahydropyridine and 5.9 g (0.0427 mol) of potassium carbonate are added. The mixture is refluxed for 6 hours, the salts formed are filtered off and the solvent is evaporated off under reduced pressure. The residue is taken up with ethyl acetate, the mixture is washed with water, the organic phase is dried over sodium sulfate and the solvent is evaporated off under reduced pressure. The residue is purified by chromatography on a silica gel column using a 7/3 cyclohexane/ethyl acetate mixture as the eluent. The fraction of Rf≈0.5 is isolated (thin layer chromatography; eluent: cyclohexane/ethyl acetate=1/1). The product with the slightly higher Rf corresponds to 1-[2-(4-methoxybiphenyl-3-yl)ethyl]-4-(3-trifluoromethylphenyl)-1,2,3,6-tetrahydropyridine, the hydrochloride of which is prepared with a saturated solution of hydrochloric acid in ethyl ether. 0.9 g is obtained. M.p.=185–187° C. (crystallized from acetone).

The product with the slightly lower Rf, corresponding to 1-[2-(4'-methoxybiphenyl-4-yl)ethyl]-4-(3-trifluoro-methylphenyl)-1,2,3,6-tetrahydropyridine, is isolated from isopropyl ether in the form of a solid. M.p.=120–123° C.

EXAMPLE 31

1-[2-(4'-Hydroxybiphenyl-4-yl)ethyl]-4-(3-trifluoro-methylphenyl)-1,2,3,6-tetrahydropyridine hydrochloride 0.5 g (1.14 mmol) of 1-[2-(4'-methoxybiphenyl-4-yl) ethyl]-4-(3-trifluoromethylphenyl)-1,2,3,6-tetrahydropyridine, prepared according to Example 30, is dissolved in 3.5 ml of 33% hydrobromic acid in acetic acid and the solution is refluxed for 3.5 hours. It is poured into ice and concentrated ammonium hydroxide solution is added to the mixture, which is extracted with ethyl acetate. The organic phase is washed with water and dried and the solvent is evaporated off under reduced pressure. The residue is purified by chromatography on a silica gel column using a 7/3 cyclohexane/ethyl acetate mixture as the eluent. The hydrochloride is prepared with a saturated solution of hydrochloric acid in ethyl ether to give 0.43 g of the title product, which is crystallized from 95% ethanol. M.p.=248–254° C.

EXAMPLE 32

1-[2-(4'-Ethoxycarbonylbutoxybiphenyl-4-yl)ethyl]-4-(3-trifluoromethylphenyl)-1,2,3,6-tetrahydropyridine hydrochloride A mixture of 400 mg (0.9 mmol) of the product of Example 31 (free base), 5 ml of DMSO and 49 mg of 60% sodium hydride is stirred at room temperature for 2 hours. 46 mg of potassium iodide and 0.17 ml (1 mmol) of ethyl 1-bromobutyrate are added. The mixture is stirred at room temperature for 2 hours, poured into water and extracted with ethyl acetate. The organic phase is washed with water and dried over sodium sulfate and the solvent is evaporated off under reduced pressure. The residue is purified by chromatography on a silica gel column using an 8/2 cyclohexane/ethyl acetate mixture as the eluent. The hydrochloride is prepared with a saturated solution of hydrochloric acid in an ethyl ether/isopropanol mixture to give the title compound. M.p.=242–247° C.

EXAMPLE 33

1-[2-(Biphenyl-3-yl)ethyl]-4-(3-trifluoromethylphenyl)-1,2,3,6-tetrahydropyridine hydrochloride 33a/2-(Biphenyl-3-yl)ethanol The title compound is obtained by following the procedure described in Example 23b but using 3-bromophenethyl alcohol instead of (3-chloro-4-trifluoromethylsulfonylphenyl)acetic acid ester and benzeneboronic acid instead of 3-chlorobenzeneboronic acid. M.p.=58–60° C.

33b/2-(Biphenyl-3-yl)ethyl p-toluenesulfonate 0.7 g (3.5 mmol) of the product of the previous step and 1 g (5.2 mmol) of tosyl chloride in 5 ml of pyridine are stirred at room temperature overnight. The mixture is poured into 1 N hydrochloric acid solution and extracted with ethyl acetate. The organic phase is washed with 3 M sodium hydroxide solution. It is dried over sodium sulfate and evaporated under reduced pressure. The residue is purified by chromatography on a silica gel column using a 9/1 and then 8/2 cyclohexane/ethyl acetate mixture as the eluent to give the title compound in the form of an oil.

33c/1-[2-(Biphenyl-3-yl)ethyl]-4-(3-trifluoromethyl-phenyl)-1,2,3,6-tetrahydropyridine hydrochloride The title compound is obtained by following the procedure described in Example 1d but using the product of the previous step instead of 2-(4-isobutylphenyl)propyl methanesulfonate. M.p.=191–192° C.

EXAMPLE 34

1-[2-(3'-Chloro-4'-fluorobiphenyl-4-yl)ethyl]-4-(3-tri-fluoromethylphenyl)-1,2,3,6-tetrahydropyridine hydrochloride 34a/2-(3I-Chloro-4'-fluorobiphenyl-4-yl)ethanol The title compound is obtained by following the procedure described in Example 23b but using 2-(p-bromophenyl) ethanol instead of ethyl (3-chloro-4-trifluoro-methylsulfonylphenyl)acetate and 3-chloro-4-fluorobenzeneboronic acid instead of 3-chlorobenzeneboronic acid.

34b/2-(3'-Chloro-4'-fluorobiphenyl-4-yl)ethyl methanesulfonate

The title compound is obtained by following the procedure described in Example 1c but using the product of the previous step instead of 2-(4-isobutylphenyl)propyl alcohol.

34c/1-[2-(3'-Chloro-4'-fluorobiphenyl-4-yl)ethyl]-4-(3-trifluoromethylphenyl)-1,2,3,6-tetrahydropyridine hydrochloride The title compound is obtained by following the procedure described in Example 1d but using the product of the previous step instead of 2-(4-isobutylphenyl)propyl methanesulfonate. M.p.=218–22° C.

EXAMPLE 35

1-[2-(2'-Trifluoromethylbiphenyl-4-yl)ethyl]-4-(3-trifluoromethylphenyl)-1,2,3,6-tetrahydropyridine hydrochloride 35a/2-(4-Bromophenyl)-2,2-dimethoxyethane A mixture of 2 g (0.01 mol) of 4-bromoacetophenone, 5.6 ml of trimethylorthoformate, 5.6 ml of methanol and 0.67 g of Amberlite® IR 120 is refluxed for 3 hours. After cooling, it is filtered on Celite and the filtered solution is evaporated to give 2.4 g of the title product in the form of an oil.

35b/2,2-Dimethoxy-2-(2'-trifluoromethylbiphenyl-4-yl) ethane

The title compound is obtained by following the procedure described in Example 23b but using the product of the previous step instead of ethyl (2,3'-dichlorobiphenyl-4-yl) acetate and 2-trifluoromethylphenylbenzeneboronic acid instead of 3-chlorobenzeneboronic acid.

35c/4-(2-Trifluoromethylphenyl)acetophenone

A solution of 4 ml of trifluoroacetic acid and 4 ml of water is added at 0° C. to a solution of 4.6 g (0.0105 mol) of the product of the previous step in 4 ml of methylene chloride. The mixture is stirred at room temperature for 2 hours, poured into water and extracted with methylene chloride. The organic phase is dried and filtered and the solvent is evaporated off under reduced pressure. The crude product is purified by chromatography on a silica gel column using a 9/1 cyclohexane/ethyl acetate mixture as the eluent to give 1.97 g of the title product.

35d/α-Bromo-4-(2-trifluoromethylphenyl)acetophenone 0.38 ml (7.5 mmol) of bromine is added dropwise at a temperature of 0° C. to a solution of 1.97 g (7.5 mmol) of the product of the previous step in 5.4 ml of methanol. The mixture is stirred at room temperature for 3 hours, the solvent is evaporated off, the residue is taken up with water and the mixture is extracted with ethyl acetate. The organic phase is dried over sodium sulfate and filtered and the solvent is evaporated off under reduced pressure to give 2.3 g of the title product.

35e/1-Bromo-2-(2'-trifluoromethylbiphenyl-4-yl)ethane 1.2 g (3.5 mmol) of the product of the previous step, 4.4 ml of trifluoroacetic acid and 2.3 ml of triethylsilane are mixed and the mixture is refluxed for 3 hours. It is then poured into a mixture consisting of concentrated sodium hydroxide solution and ice, the reaction medium is extracted with ethyl acetate, the organic phase is dried over sodium sulfate and the solvent is evaporated off under reduced pressure to give the title compound.

35f/1-[2-(2'-Trifluoromethylbiphenyl-4-yl)ethyl]-4-(3-trifluoromethylphenyl)-1,2,3,6-tetrahydropyridine hydrochloride The title compound is obtained by following the procedure described in Example 1d but using the product of the previous step instead of 2-(4-isobutylphenyl)propyl methanesulfonate. M.p.=176–178° C.

EXAMPLE 36

1-[2-(3,4-Diisobutylphenyl)ethyl]-4-(3-trifluoromethyl-phenyl)-1,2,3,6-tetrahydropyridine oxalate 36a/1,2-Diisobutylbenzene A solution of 9.4 g (0.07 mol) of 1,2-diphthalaldehyde in 30 ml of THF is added dropwise under a nitrogen atmosphere to a 2 M solution of isopropylmagnesium chloride in THF. The mixture is then stirred at room temperature for 2 hours and poured into saturated ammonium chloride solution, the THF is evaporated off under reduced pressure and the residue is extracted with ethyl ether. The organic phase is dried over sodium sulfate and the solvent is evaporated off under reduced pressure. The residue is purified by chromatography on a silica gel column using a 7/3 cyclohexane/ethyl acetate mixture as the eluent. The resulting diol is dissolved in 110 ml of absolute ethanol, and 5 ml of 96% sulfuric acid and 0.67 g of 10% Pd/C are added. The mixture is hydrogenated at atmospheric pressure and room temperature. After the theoretical amount of hydrogen has been consumed (about 7 hours), the catalyst is filtered off, the solvent is evaporated off, the residue is taken up with ethyl acetate, the mixture is washed with aqueous bicarbonate solution and then with water, the organic phase is dried and the solvent is evaporated off under reduced pressure to give 3.9 g of the title compound in the form of an oil.

36b/1-Bromo-2-(3,4-diisobutylphenyl)ethane

The title compound is obtained by following the procedure described in Example 4a but using the product of the previous step instead of isobutylbenzene.

36c/1-[2-(3,4-Diisobutylphenyl)ethyl]-4-(3-trifluoro-methylphenyl)-1,2,3,6-tetrahydropyridine oxalate The title compound is obtained by following the procedure described in Example 4b but using the product of the previous step instead of 1-bromo-2-(4-isobutylphenyl) ethane and treating the resulting base with oxalic acid instead of hydrochloric acid. M.p.=175–178° C.

EXAMPLE 37

1-[2-(3,4-Dipropylphenyl)ethyl]-4-(3-trifluoromethyl-phenyl)-1,2,3,6-tetrahydropyridine oxalate 37a/1,2-Dipropylbenzene The title compound is obtained by following the procedure described in Example 36a but using 1,2-dicarboxyaldehyde instead of 1,2-diphthalaldehyde.

37b/1-Bromo-2-(3,4-dipropylphenyl)ethane

The title compound is obtained by following the procedure described in Example 36b but using the product of the previous step instead of 1,2-diisobutylbenzene.

37c/1-[2-(3,4-Dipropylphenyl)ethyl]-4-(3-trifluoro-methylphenyl)-1,2,3,6-tetrahydropyridine oxalate The title compound is obtained by following the procedure described in Example 36c but using the product of the previous step instead of 1-bromo-2-(3,4-diisopropylphenyl) ethane. M.p. =180–182° C.

EXAMPLE 38
1-[2-(4-Cyclohexylphenyl)ethyl]-4-(6-chloropyrid-2-yl)-1,2,3,6-tetrahydropyridine The title compound is obtained by following the procedure described in Example 22d but using 1-bromo-2-(4-cyclohexylphenyl)ethane (prepared according to Example 19a) instead of 4-(2-bromoethyl)biphenyl.

EXAMPLE 39
1-[2-(4-Isobutylphenyl)propyl]-4-(6-chloropyrid-2-yl)-1,2,3,6-tetrahydropyridine hydrochloride The title compound is obtained by following the procedure described in Example 1d but using 4-(6-chloropyrid-2-yl)-1,2,3,6-tetrahydropyridine (prepared according to Example 22c) instead of 4-(3-trifluoromethylphenyl)-1,2,3,6-tetrahydropyridine. M.p.=185–190° C.

We claim:

1. A compound of formula (I):

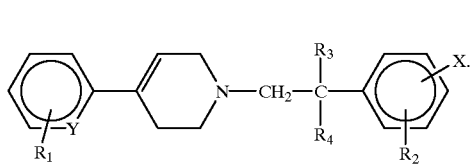

(I)

in which

Y is —CH— or —N—;

$R_1$ is hydrogen, a halogen atom, a $CF_3$ group, a $(C_3–C_4)$alkyl or a $(C_1–C_4)$alkoxy group;

$R_2$ is hydrogen, a halogen atom, a hydroxy group, a $CF_3$ group, a $(C_3–C_4)$alkyl or a $(C_{1-C4})$alkoxy group;

$R_3$ and $R_4$ are each hydrogen or a $(C_1–C_3)$alkyl group; and

X is (a) a $(C_3–C_6)$alkyl group, a $(C_3–C_6)$alkoxy group, a $(C_3–C_7)$carboxyalkyl group, a $(C_1–C_4)$alkoxycarbonyl$(C_3–C_6)$alkyl group, a $(C_3–C_7)$carboxyalkoxy group or a $(C_1–C_4)$alkoxycarbonyl$(C_3–C_6)$alkoxy group;

(b) a $(C_3–C_7)$cycloalkyl group, a $(C_3–C_7)$cycloalkoxy group, a $(C_3–C_7)$cycloalkylmethyl group, a $(C_3–C_7)$ cycloalkylamino group or a cyclohexenyl group, it being possible for said group to be substituted by a halogen atom, a hydroxyl group, a $(C_1–C_4)$alkoxy group, a carboxyl group, a $(C_1–C_4)$alkoxycarbonyl group, an amino group or a mono- or di-$(C_1–C_4)$ alkylamino group; or (c) a phenyl group, a phenoxy group, a phenylamino group, a N-$(C_1–C_3)$alkylphenylamino group, a phenyl-methyl group, a phenylethyl group, a phenylcarbonyl group, a phenylthio group, a phenylsulfonyl group, a phenylsulfinyl group or a styryl group, it being possible for said group to be monosubstituted or polysubstituted on the phenyl group by a halogen atom, a $CF_3$ group, a $(C_1–C_4)$alkyl group, a $(C_1–C_4)$alkoxy group, a cyano group, an amino group, a mono- or di-$(C_1–C_4)$ alkylamino group, a $(C_1–C_4)$acylamino group, a carboxyl group, a $(C_1–C_4)$alkoxycarbonyl group, an aminocarbonyl group, a mono- or a di-$(C_1–C_4)$ alkylaminocarbonyl group, an amino $(C_1–C_4)$alkyl group, a hydroxy$(C_1–C_4)$alkyl group or a halogeno $(C_1–C_4)$alkyl group;

a salt, solvate or a quaternary ammonium salt thereof.

2. A compound according to claim 1 in which X is in the 4-position of the phenyl group.

3. A process for the preparation of a compound of formula (I) of claim 1, a salt, solvate or a quaternary ammonium salt thereof, which comprises (a) reacting an aryl-1,2,3,6-tetrahydropyridine of formula (II):

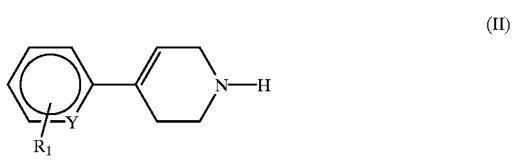

(II)

in which Y and $R_1$ are as defined for (I) in claim 1, with a compound of formula (III)

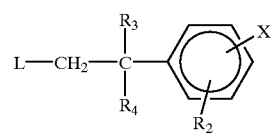

(III)

in which $R_2$, $R_3$, $R_4$ and X are as defined for (I) in claim 1 and L is a leaving group; and (b) isolating the resulting compound of formula (I) and optionally converting it to a salt, solvate or a quaternary ammonium salt thereof.

4. A process for the preparation of a compound formula (I) of claim 1 in which Y is —CH—, a salt, solvate or a quaternary ammonium salt thereof, which comprises (a) reacting a compound of formula (IV):

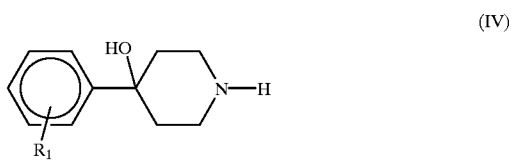

(IV)

in which $R_1$ is as defined for (I) in claim 1, with a functional derivative of the acid of formula (V):

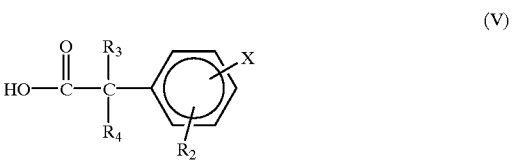

(V)

in which $R_2$, $R_3$, $R_4$ and X are as defined for (I) in claim 1

(b) reacting the carbonyl group of the resulting compound of formula (VI):

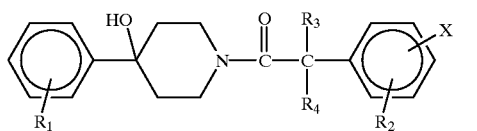

(VI)

(c) dehydrating the resulting intermediate piperidinol of formula (VII):

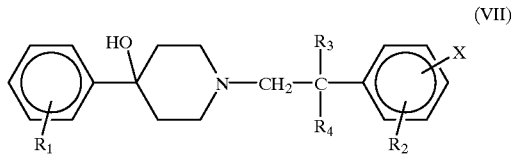

(VII)

and (d) isolating the resulting compound of formula (I) and optionally converting it to a salt, solvate or a quaternary ammonium salt thereof.

5. A compound of formula (i):

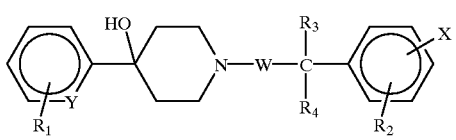

(i)

in which

Y is —CH— or —N—;

$R_1$ is hydrogen, a halogen atom, a $CF_3$ group, a $(C_3-C_4)$alkyl group or a $(C_1-C_4)$alkoxy group;

$R_2$ is hydrogen, a halogen atom, a hydroxyl group, a $CF_3$ group, a $(C_3-C_4)$alkyl group or a $(C_1-C_4)$alkoxy group;

$R_3$ and $R_4$ are each hydrogen or a $(C_1-C_3)$alkyl group; and X is (a) a $(C_3-C_6)$alkyl group, a $(C_3-C_6)$alkoxy group, a $(C_3-C_7)$carboxyalkyl group, a $(C_1-C_4)$alkoxycarbonyl $(C_3-C_6)$alkyl group, a $(C_3-C_7)$carboxyalkoxy group, or a $(C_1-C_4)$alkoxycarbonyl$(C_3-C_6)$alkoxy group;

(b) a $(C_3-C_7)$cycloalkyl group, a $(C_3-C_7)$cycloalkoxy group, a $(C_3-C_7)$cycloalkylmethyl group, a $(C_3-C_7)$ cycloalkylamino group or a cyclohexenyl group, it being possible for said group to be substituted by a halogen atom, a hydroxyl group, a $(C_1-C_4)$alkoxy group, a carboxyl group, a $(C_1-C_4)$alkoxycarbonyl group, an amino group or a mono- or di-$(C_1-C_4)$ alkylamino group; or (c) a phenyl group, a phenoxy group, a phenylamino group, a N-$(C_1-C_3)$alkylphenylamino group, a phenylmethyl group, a phenylethyl group, a phenylcarbonyl group, a phenylthio group, a phenylsulfonyl group, a phenylsulfinyl group or a styryl group, it being possible for said group to be monosubstituted or polysubstituted on the phenyl group by a halogen atom, a $CF_3$ group, a $(C_1-C_4)$alkyl group, a $(C_1-C_4)$alkoxy group, a cyano group, an amino group, a mono- or di-$(C_1-C_4)$ alkylamino group, a $(C_1-C_4)$acylamino group, a carboxyl group, a $(C_1-C_4)$alkoxycarbonyl group, an aminocarbonyl group, a mono- or a di-$(C_1-C_4)$ alkylaminocarbonyl group, an amino $(C_1-C_4)$alkyl group, a hydroxy$(C_1-C_4)$alkyl group or a halogeno $(C_1-C_4)$alkyl group;

W is a methylene group or a carbonyl group, or a salt thereof.

6. A process for the preparation of a compound of formula (t'):

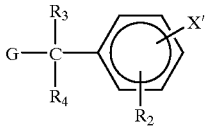

(t')

in which $R_2$ is hydrogen, a halogen atom, a hydroxyl group, a $CF_3$ group, a $(C_3-C_4)$alkyl group or a $(C_1-C_4)$alkoxy group;

$R_3$ and $R_4$ are each hydrogen or a $(C_1-C_3)$alkyl group, and

X' is a phenyl group optionally monosubstituted or polysubstituted by a halogen atom, a $CF_3$ group, a $(C_1-C_4)$alkyl group, a $(C_1-C_4)$alkoxy group, a cyano group, an amino group, a mono- or di-$(C_1-C_4)$alkylamino group, a $(C_1-C_4)$acylamino group, a carboxyl group, a $(C_1-C_4)$ alkoxycarbonyl group, an aminocarbonyl group, a mono- or a di-$(C_1-C_4)$aklylaminocarbonyl group, an amino $(C_1-C_4)$alkyl group, a hydroxy$(C_1-C_4)$alkyl group, or a halogeno$(C_1-C_4)$alkyl group, G is a carboxyl group or a group L—CH$_2$—, in which L is a leaving group, which process comprises reacting a compound of formula (w'):

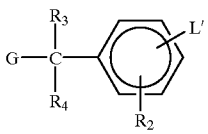

(w')

in which $R_2$, $R_3$, $R_4$ and G are defined above and L' is a leaving group, with a benzeneboronic acid having a formula X'-B(OH)$_2$, in which X' is as defined above, in the presence of a palladium salt, a strong base and a phase transfer agent, in an aqueous medium.

7. A process according to claim 6 wherein the leaving group L' is bromine or the trifluoromethylsulfonyloxy group.

8. A process according to claim 6 wherein the palladium salt used is palladium acetate.

9. A process according to claim 7 wherein the palladium salt used is palladium acetate.

10. A process according to claim 6 wherein the strong base used is an alkali metal hydroxide or a carbonate.

11. A process according to claim 7 wherein the strong base used is an alkali metal hydroxide or a carbonate.

12. A process according to claim 8 wherein the strong base used is an alkali metal hydroxide or a carbonate.

13. A process according to claim 6 wherein the phase transfer agent is a tetraalkylammonium halide.

14. A process according to claim 7 wherein the phase transfer agent is a tetraalkylammonium halide.

15. A process according to claim 8 wherein the phase transfer agent is a tetraalkylammonium halide.

16. A process according to claim 10 wherein the phase transfer agent is a tetraalkylammonium halide.

17. A process according to claim 6 wherein the reaction is carried out at a temperature between 30° C. and the reflux point.

18. A process according to claim 7 wherein the reaction is carried out at a temperature between 30° C. and the reflux point.

19. A process according to claim 8 wherein the reaction is carried out at a temperature between 30° C. and the reflux point.

20. A process according to claim 10 wherein the reaction is carried out at a temperature between 30° C. and the reflux point.

21. A process according to claim 13 wherein the reaction is carried out at a temperature between 30° C. and the reflux point.

22. A process for the preparation of the compound of formula (t):

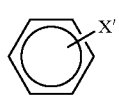

(t)

in which the benzene group can optionally be substituted and X' is a phenyl group optionally monosubstituted or polysubstituted by a halogen atom, a $CF_3$ group, a $(C_1-C_4)$ alkyl group, a $(C_1-C_4)$alkoxy group, a cyano group, an amino group, a mono- or di-$(C_1-C_4)$alkylamino group, a $(C_1-C_4)$acylamino group, a carboxyl group, a $(C_1-C_4)$ alkoxycarbonyl group, an aminocarbonyl group, a mono- or a di-$(C_1-C_4)$alkylaminocarbonyl group, an amino$(C_1-C_4)$ alkyl group, a hydroxy$(C_1-C_4)$alkyl group or a halogeno $(C_1-C_4)$ alkyl group, said process comprising reacting a compound of formula (w):

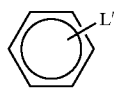

(w)

in with the benzene group can optionally be substituted and L' is a leaving group, which a benezeneboronic acid of the formula X'—B(OH)$_2$, in which X' is as defined above, in the presence of a palladium salt, a strong base and a phase transfer agent, in an aqueous medium.

23. A process according to claim 22 wherein the leaving group L' is bromine or the trifluoromethylsulfonyloxy group.

24. A process according to claim 22 wherein the palladium salt used is palladium acetate.

25. A process according to claim 22 wherein the strong base used is selected from alkali metal hydroxides and carbonates.

26. A process according to claim 22 wherein the phase transfer agent is a tetraalkylammonium halide.

27. A process according to claim 22 wherein the reaction is carried out at a temperature between 30° C. and the reflux point.

28. A process according to claim 23 wherein the palladium salt used is palladium acetate.

29. A process according to claim 23 wherein the strong base used is an alkali metal hydroxide or a carbonate.

30. A process according to claim 24 wherein the strong base used is an alkali metal hydroxide or a carbonate.

31. A process according to claim 23 wherein the phase transfer agent is a tetraalkylammonium halide.

32. A process according to claim 24 wherein the phase transfer agent is a tetraalkylammonium halide.

33. A process according to claim 25 wherein the phase transfer agent is a tetraalkylammonium halide.

34. A process according to claim 23 wherein the reaction is carried out at a temperature between 30° C. and the reflux point.

35. A process according to claim 24 wherein the reaction is carried out at a temperature between 30° C. and the reflux point.

36. A process according to claim 25 wherein the reaction is carried out at a temperature between 30° C. and the reflux point.

37. A process according to claim 26 wherein the reaction is carried out at a temperature between 30° C. and the reflux point.

38. A compound of formula (II'):

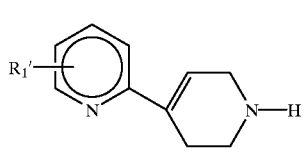

(II')

in which $R_1$' is a halogen atom, a $CF_3$ group, a $(C_3-C_4)$alkyl group or a $(C_1-C_4)$alkoxy group or a salt thereof.

39. A compound according to claim 1 in which X is a group (c) in which the phenyl group is substituted by 1 to 3 halogen atoms, 1 to 3 $CF_3$ groups, 1 to 3 $(C_1-C_4)$alkyl groups, 1 to 3 $(C_1-C_4)$alkoxy groups, 1 to 3 cyano groups, 1 to 3 amino groups, 1 to 3 mono- or di-$(C_1-C_4)$alkylamino groups, 1 to 3 $(C_1-C_4)$acylamino groups, 1 to 3 carboxyl groups, 1 to 3 $(C_1-C_4)$alkoxycarbonyl groups, 1 to 3 aminocarbonyl groups, 1 to 3 mono- or di-$(C_1-C_4)$ alkylaminocarbonyl groups, 1 to 3 amino$(C_1-C_4)$alkyl groups, 1 to 3 hydroxy$(C_1-C_4)$alkyl groups or 1 to 3 halogeno$(C_1-C_4)$alkyl groups.

40. A compound according to claim 2 in which X is a group (c) in which the phenyl group is substituted by 1 to 3 halogen atoms, 1 to 3 $CF_3$ groups, 1 to 3 $(C_1-C_4)$alkyl groups, 1 to 3 $(C_1-C_4)$alkoxy groups, 1 to 3 cyano groups, 1 to 3 amino groups, 1 to 3 mono- or di-$(C_1-C_4)$alkylamino groups, 1 to 3 $(C_1-C_4)$acylamino groups, 1 to 3 carboxyl groups, 1 to 3 $(C_1-C_4)$alkoxycarbonyl groups, 1 to 3 aminocarbonyl groups, 1 to 3 mono- or di-$(C_1-C_4)$ alkylaminocarbonyl groups, 1 to 3 amino$(C_1-C_4)$alkyl groups, 1 to 3 hydroxy$(C_1-C_4)$alkyl groups or 1 to 3 halogeno$(C_1-C_4)$alkyl groups.

41. A pharmaceutical composition which contains (i) an effective amount of a compound according to claim 1, a pharmaceutically acceptable salt or solvate thereof or a pharmaceutically acceptable quaternary ammonium salt thereof, and (ii) at least one pharmaceutically acceptable excipient.

42. A pharmaceutical composition according to claim 41, which contains from 0.5 to 700 mg of said compound.

43. A pharmaceutical composition which contains (i) an effective amount of a compound according to claim 2, a pharmaceutically acceptable salt or solvate thereof or a pharmaceutically acceptable quaternary ammonium salt thereof, and (ii) at least one pharmaceutically acceptable excipient.

44. A pharmaceutical composition according to claim 43, which contains from 0.5 to 700 mg of said compound.

45. A pharmaceutical composition which contains (i) an effective amount of a compound according to claim 39, a pharmaceutically acceptable salt or solvate thereof or a pharmaceutically acceptable quaternary ammonium salt thereof, and (ii) at least one pharmaceutically acceptable excipient.

46. A pharmaceutical composition according to claim 43, which contains from 0.5 to 700 mg of said compound.

47. A pharmaceutical composition which contains (i) an effective amount of a compound according to claim 40, a pharmaceutically acceptable salt or solvate thereof or a pharmaceutically acceptable quaternary ammonium salt thereof, and (ii) at least one pharmaceutically acceptable excipient.

48. A pharmaceutical composition according to claim 47, which contains from 0.5 to 700 mg of said compound.

49. A compound according to claim 2, which is 1-[2-(biphenyl-4-yl)ethyl]-4-(3-trifluoromethylphenyl)-1,2,3,6-tetrahydropyridine, a salt or a solvate thereof.

50. A pharmaceutical composition comprising (i) an effective amount of a compound according to claim 49, a pharmaceutically acceptable salt or solvate thereof, and (ii) at least one pharmaceutically acceptable excipient.

51. A pharmaceutical composition according to claim 50, comprising from 0.5 to 700 mg of said compound.

* * * * *